(12) United States Patent
Lagu et al.

(10) Patent No.: US 7,262,197 B2
(45) Date of Patent: Aug. 28, 2007

(54) PHOSPHOLIPASE C INHIBITORS FOR USE IN TREATING INFLAMMATORY DISORDERS

(75) Inventors: Bharat Lagu, Hillsborough, NJ (US); Kenneth Rupert, South Orange, NJ (US); Michael Wachter, Bloomsbury, NJ (US)

(73) Assignee: Janssen Pharmaceutica, N.V, Beerse (BE)

( * ) Notice: Subject to any disclaimer, the term of this patent is extended or adjusted under 35 U.S.C. 154(b) by 359 days.

(21) Appl. No.: 10/815,048

(22) Filed: Mar. 31, 2004

(65) Prior Publication Data

US 2004/0235827 A1 Nov. 25, 2004

Related U.S. Application Data

(60) Provisional application No. 60/459,067, filed on Mar. 31, 2003.

(51) Int. Cl.
 *A61K 31/496* (2006.01)
 *C07D 295/155* (2006.01)
 *C07D 307/68* (2006.01)
 *A61K 31/551* (2006.01)

(52) U.S. Cl. ............ 514/252.11; 544/357; 544/360; 544/379; 544/377; 540/575

(58) Field of Classification Search ........... 544/357, 544/379
See application file for complete search history.

(56) References Cited

U.S. PATENT DOCUMENTS 6,906,073 B2 * 6/2005 Du Bois et al. ......... 514/252.13

FOREIGN PATENT DOCUMENTS

| WO | WO96/10568 | 4/1996 |
| WO | 98/27081 | * 6/1998 |
| WO | WO 02/32867 | 4/2002 |

OTHER PUBLICATIONS

Chemical Abstract, Database—Chemcats, Catalog Name, Otava Stock Chemicals, Chemical Abstract Service, Columbus, Ohio, Order Nos. 7114960248, 7114960239, 7114960244 and 7114960243, Sep. 24, 2003.

* cited by examiner

*Primary Examiner*—Emily Bernhardt
(74) *Attorney, Agent, or Firm*—Thomas Dodd

(57) ABSTRACT

This invention is directed to heterocyclyl-substituted anilino phospholipase C inhibitor compounds useful in treating or ameliorating an inflammatory disorders and/or restenosis of the general formula (I):

formula (I)

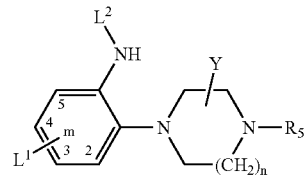

and enantiomers, diastereomers and pharmaceutically acceptable salts thereof. The present invention is further directed to pharmaceutical compositions comprising the compounds of the present invention and to methods for treating conditions affected by phospholipase modulation.

2 Claims, No Drawings

PHOSPHOLIPASE C INHIBITORS FOR USE IN TREATING INFLAMMATORY DISORDERS

CROSS REFERENCE TO RELATED APPLICATIONS

This present application claims benefit of U.S. Provisional Patent Application Ser. No. 60/459,067, filed Mar. 31, 2003, which is incorporated herein by reference in its entirety and for all purposes.

FIELD OF THE INVENTION

This invention relates to a series of phosphoinositide-specific phospholipase C (PLC) inhibitors useful in treating or ameliorating an inflammatory disorder. More particularly, the PLC inhibitors are heterocyclyl-substituted anilino compounds useful in treating or ameliorating an inflammatory disorder.

BACKGROUND OF THE INVENTION

Phosphoinositide-specific phospholipase C class enzymes are involved in many signaling pathways in which a cellular response (such as proliferation or secretion) is produced consequent to an extracellular stimulus. Distinct isozymes of PLC have been isolated, purified, and/or molecularly cloned from a variety of mammalian tissues. Classified on the basis of their deduced amino acid sequence, the distinct types of PLC isozymes have been identified as PLC-beta, PLC-gamma and PLC-delta (four distinct types of PLC isozymes were originally isolated and identified as PLC-alpha, PLC-beta, PLC-gamma and PLC-delta; the subtypes within the groups were named using Arabic numerals: PLC-β1, PLC-β2, PLC-β3 and PLC-β4 (Rhee, S. G., Suh, P., Ryu, S. & Lee, S. Y., Studies of Inositol Phosphalipid-Specific Phospholipase C, *Science*, 1989, 244:546-50). PLC-alpha was later determined to be in the PLC-delta class (Rhee S. G. & Choi, K. D., Regulation of Inositol Phospholipid-Specific Phospholipase C Isozymes, *Journal of biological Chemistry*, 1992, 267:12393-96).

The subtypes differ in their ability to hydrolyze phosphatidylinositol (PI), phosphatidylinositol-4-phosphate (PIP) or phosphatidylinositol-4,5-bisphosphate (PIP2) and in their dependence on $Ca^{2+}$. PIP2 is the main source of phospholipid second messengers and is stored in the inner leaflet of the plasma membrane. PIP2 is derived from PI by a series of kinases. PI is synthesized in the endoplasmic reticulum and is transferred to the inner plasma membrane. PI can also be further phosphorylated by PI-4-kinase, which is membrane associated in most tissues, to give PIP. Finally, PIP can also be phosphorylated by PI(4)P-5-kinases to generate PIP2 (Rhee S. G., Regulation of Phosphoinositide-Specific Phospholipase C, *Ann. Rev. Biochem.*, 2001, 70:221-312, Majerus, Philip W., Inositol Phosphate Biochemistry, *Annual Review of Biochemistry*, 1992, 61:225-50).

Recruitment and activation of leukocytes are essential components of the inflammatory response. The inflammatory response is primarily controlled by two groups of proteins known as chemokines (e.g. MCP-1 (monocyte chemotactic protein-1)) and cytokines (e.g. tumor necrosis factor-α [TNF-α] or interleukin-1 [IL-1]) (Feng L., Role of Chemokines in Inflammation and Immunoregulation, *Immunol. Res.*, 2000, 21:203-210). Resident tissue cells secrete chemokines and cytokines following tissue injury and/or the detection of the presence of an infectious agent (Gerard C., Rolling B., Chemokines and Disease, *Nat. Immunol.*, 2000, 2:108-115).

Several cytokines (e.g., IL-1 and TNF-α) stimulate vascular endothelial cells to upregulate their expression of adhesion molecules for circulating leukocytes, while chemokines direct the movement of the leukocytes through the endothelial barrier to the site of inflammation and activate such cells once they have migrated into the lesion (Keane M. P., Strieter R. M., Chemokine Signaling in Inflammation, *Crit. Care Med.*, 2000, 28:Suppl 4, N13-N26). Although inflammation plays a critical role in host defense to microorganisms, a poorly-regulated inflammatory response is a primary factor in the pathophysiology of several prevalent autoimmune diseases, has been implicated in the recruitment and activation of mononuclear cells in the synovial membrane in patients with rheumatoid arthritis (RA), and appears to stimulate cartilage and bone destruction. For example, the concentrations of MCP-1 (MCP-1 stimulates the upregulation of adhesion molecules on the surface of monocytes, thereby enhancing their ability to adhere to vascular endothelium, their migratory capacity and their production of superoxide anion, an essential factor in the process of killing phagocytized bacteria (Keane , 2000), MIP-1α, (macrophage inflammatory protein-1α), TNF-α and other chemokines and cytokines are increased in the inflamed joints of patients with RA, with higher levels correlating with increased severity of the disease in both man and experimental animals (Ellingsen T., et al, Plasma MCP-1 is a Marker for Joint Inflammation in Rheumatoid Arthritis, *J. Rheumatol.*, 2001, 28:41-46; Hjelmstrom P., et al, Lymphoid Tissue Homing Chemokines are Expressed in Chronic Inflammation, *Am. J. Pathol.*, 2000, 156:1133-1138; and, Kasama T., et al, Interleukin-10 Expression and Chemokine Regulation During the Evolution of Murine Type ii Collagen-Induced Arthritis, *J. Clin. Invest.*, 1995, 95:2868-2876).

Chemokines also appear to be important mediators in multiple sclerosis (MS). Chemokine concentrations are elevated in the CSF (cerebrospinal fluid) of MS patients, and central nervous system T-cells in MS patients are highly enriched for certain chemokine receptors (Sorensen T. L., et al, Expression of Specific Chemokines and Chemokine Receptors in the Central Nervous System of Multiple Sclerosis Patients, *J. Clin. Invest.*, 1999, 103:807-815). Mice deficient in MCP-1 or CCR2 (the cell-surface receptor for MCP-1) are resistant to the development of experimental autoimmune encephalomyelitis (EAE), a well-characterized animal model of MS (Fife B. T., et al, CC Chemokine Receptor 2 is Critical for Induction of Experimental Autoimmune Encephalomyelitis, *J. Exp. Med.*, 2002, 192:899-905; and Huang D., et al, Absence of Monocyte Chemoattractant-1 in Mice Leads to Decreased Local Macrophage Recruitment and Antigen-Specific T Helper Cell Type 1 Immune Response in Experimental Allergic Encephalomyelitis, *J. Exp. Med.*, 2000, 193:713-725).

Many chemokines (eg interleukin-8 [IL-8]) interact with cell-surface receptors to stimulate PLCβ2 via receptor-linked G-proteins (guanine-nucleotide binding proteins) (Kriz D., et al, Ciba Found, *Symp.*, 1990, 150:112-117). Activation of PLC-β2 by the receptor-linked G-protein catalyzes the hydrolysis of PIP2 to release the second messengers 1,2-diacylglycerol (DAG) and 1,4,5-inositol trisphosphate (IP3). IP3 stimulates intracellular $Ca^{2+}$ release, while hydrophobic DAG remains in the plasma membrane where it mediates the activation of members of the protein kinase C ("PKC") family. PLC-β2 is found primarily in hematopoietic cells and can be activated by both the $G_\alpha$ subunits of the $G_q$ class and by the $\beta\gamma$ subunits generated by a number of different G-proteins (Park D., et al, Cloning, Sequencing, Expression and $G_q$-Independent Activation of Phospholipase C-$\beta$2, *J. Biol. Chem.*, 1992, 267: 16048-16055).

Cotransfection experiments in COS-7 and HEK 293 cells demonstrate clearly that PLC-$\beta$2 functions downstream of several chemokine receptors (Wu D., Roles of Phospholipid Signaling in Chemoattractant-Induced Responses, *J. Cell Sci.*, 2000, 113:2935-2940; Huping J., et al, Role of Phospholipase C-$\beta$2 in Chemoattractant-Elicited Responses, *Proc. Natl. Acad. Sci.* (USA), 1997, 94:7971-7975).

For example, experiments with cells expressing transfected receptors for complement component C5a, fMet-Leu-Phe (fMLP) (Sigma, catalog no. F-3506), IL-8 or MCP-1 have shown that each of these receptors activates PLC-$\beta$2 through a pertussis toxin (PTx)-sensitive mechanism to release $\beta\gamma$ subunits from the $G_i$ class of heterotrimeric G-proteins (Jiang H, et al, Pertussis Toxin-Sensitive Activation of Phospholipase C by the C5a and fMet-Leu-Phe Receptors, *J. Biol. Chem.*, 1996, 271:13430-13434). Additional evidence for the involvement of PLC-$\beta$2 in signaling through chemokine receptors comes from experiments in knockout (KO) mice deficient in expression of the PLC-$\beta$2 protein. Although hematopoeisis is not affected in these mice, cells from the mice have decreased responsiveness to chemokines as measured by $Ca^{2+}$ fluxes, generation of inositol phosphates, upregulation of adhesion molecules, phosphorylation of MAP kinases and production of superoxide anion (Wu D., 2000; Huping J., 1997). Surprisingly, however, leukocytes from those mice were reported to have normal or even enhanced chemotactic responses to various chemokines (Park D., 2000; Wu D., 2000; Huping J., 1997). Inhibitors of PLC-$\beta$2 enzymatic activity inhibit chemotactic responses to various chemotactic factors, suggesting that a compensatory mechanism may exist in the PLC-$\beta$2 KO mice which overcomes the congenital absence of the enzyme to allow normal or enhanced migratory responsiveness to chemokines (Park D., 2000; Wu D., 2000; Huping J., 1997).

References to a number of substituted piperazine and piperidine compounds include those disclosing use as an inhibitor of the NHE1 isoform of the sodium/hydrogen exchanger (Lorrain, J., et al; Pharmacological Profile of SL 591227, A Novel Inhibitor of the Sodium/Hydrogen Exchanger, *Brit. J. Pharm.*, 2000, 131:1188-1194), as platelet aggregation inhibitors (acting as fibrinogen receptor antagonists) (U.S. Pat. No. 5,795,893), as tachykinin receptor antagonists (U.S. Pat. No. 5,607,936), as 5HT2C antagonists (U.S. Pat. No. 5,972,937), as 5HT1D receptor antagonists (U.S. Pat. No. 5,905,080), as enzyme acyl coenzyme A: cholesterol acyltransferase inhibitors (U.S. Pat. No. 5,185,358), as protein isoprenyl tranferase (such as protein farnesyltransferase and protein geranylgeranyltransferase) inhibitors (U.S. Pat. No. 6,310,095), as cardiovascular agents (U.S. Pat. No. 5,547,966) and as antiviral agents (European Patent EP0548798). PCT application WO 93/30322 discloses thiourea compounds for treating AIDS and/or HIV.

The PLC class of enzymes play important roles in inflammatory responses. Therefore, inhibitors of PLC may be useful in treating or ameliorating inflammatory disorders. The present invention provides novel heterocyclyl-substituted anilino compounds which function as PLC inhibitors, thereby providing a means for the treatment and/or amelioration of disorders and conditions mediated by PLC-$\beta$2, including inflammatory and related disorders.

SUMMARY OF THE INVENTION

An embodiment of the present invention includes a method for treating or ameliorating disorders and conditions mediated by PLC-$\beta$2, including inflammatory disorders in a subject in need thereof comprising administering to the subject a therapeutically effective amount of a compound of formula (I).

DETAILED DESCRIPTION OF THE INVENTION

The present invention provides heterocyclyl-substituted anilino compounds useful for the treatment of disorders and conditions mediated by PLC-$\beta$2.

In particular, the heterocyclyl-substituted anilino compounds of the present invention are of the general formula (I):

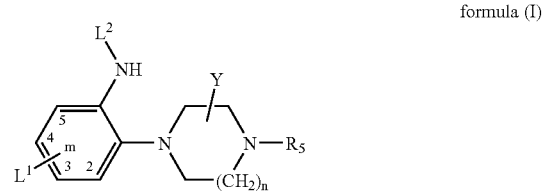

formula (I)

and enantiomers, diastereomers and pharmaceutically acceptable salts thereof, wherein:

$L^1$ is a substituent moiety having a variable position "m", wherein "m" represents a carbon atom number corresponding to a point of attachment for the $L^1$ substituent moiety on the anilino ring of formula (I);

$L^1$ is selected from the group consisting of $R_{1b}$, $R_2$—C(O), $R_{1a}$—SO$_2$ and $R_{1a}$—O(O)C—;

$R_{1a}$ is $C_{1-8}$alkyl optionally substituted with one or more substituents independently selected from the group consisting of $C_{1-8}$alkoxy, amino, mono($C_{1-8}$)alkylamino, di($C_{1-8}$)alkylamino, halogen and hydroxy;

$R_{1b}$ is $C_{1-8}$alkyl optionally substituted with one or more substituents independently selected from the group consisting of amino, mono($C_{1-8}$)alkylamino, di($C_{1-8}$)alkylamino, halogen and hydroxy;

$R_2$ is heterocyclyl optionally substituted on a nitrogen atom with $C_{1-8}$alkyl;

$L^2$ is selected from the group consisting of $R_3$—C(O)—, $R_4$—SO$_2$—, $R_6$—NHC(S)— and $R_6$—NHC(O)—;

$R_3$ is selected from the group consisting of (a) $C_{1-8}$alkyl optionally substituted with one or more substituents independently selected from the group consisting of $C_{1-8}$alkoxy, amino, mono($C_{1-4}$)alkylamino, di($C_{1-4}$)alkylamino, hydroxy, aryl and heteroaryl;

wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

(b) aryl optionally substituted with one or more substituents independently selected from the group consisting of $C_{1-8}$alkyl, $C_{1-8}$alkoxy; amino, mono($C_{1-4}$)alkylamino, di($C_{1-4}$)alkylamino, cyano, halogen, hydroxy and nitro; and, (c) heteroaryl optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro and aryl, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

$R_4$ is selected from the group consisting of (d) $C_{1-8}$alkyl optionally substituted with one or more substituents independently selected from the group consisting of C1-8alkoxy, amino, mono($C_{1-4}$)alkylamino, di($C_{1-4}$)alkylamino, hydroxy, aryl and heteroaryl; and, (e) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

$R_6$ is aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

$R_5$ is selected from the group consisting of (f) $C_{1-8}$alkyl optionally substituted with one or more aryl substituents, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro, aryl' and heteroaryl;

wherein said aryl' is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

(g) $C_{3-8}$cycloalkyl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, (h) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

Y is one or more optionally present $C_{1-8}$alkyl substituents optionally substituted with one or more substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted;

m is an integer from 2 to 5 which represents the carbon atom number corresponding to the point of attachment for the $L^1$ substituent moiety on the anilino ring of formula (I); and, n is an integer from 1 to 2.

In an embodiment of the present invention are compounds of formula (Ia):

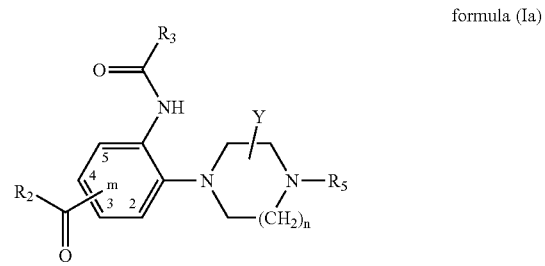

formula (Ia)

and enantiomers, diastereomers and pharmaceutically acceptable salts thereof, wherein:

$R_2$—C(O)— is a substituent moiety having a variable position "m", wherein "m" represents a carbon atom number corresponding to a point of attachment for the $R_2$—C(O)— substituent moiety on the anilino ring of formula (Ia);

$R_2$ is heterocyclyl optionally substituted on a nitrogen atom with $C_{1-8}$alkyl;

$R_3$ is selected from the group consisting of (a) $C_{1-8}$alkyl optionally substituted with one or more substituents independently selected from the group consisting of $C_{1-8}$alkoxy, amino, mono($C_{1-4}$)alkylamino, di($C_{1-4}$)alkylamino, hydroxy, aryl and heteroaryl;

wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$) alkylamino, di($C_{1-4}$)alkylamino, cyano, halogen, hydroxy and nitro;

(b) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, (c) heteroaryl optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro and aryl, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

$R_5$ is selected from the group consisting of (f) $C_{1-8}$alkyl optionally substituted with one or more aryl substituents, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro, aryl' and heteroaryl;

wherein said aryl' is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$) alkylamino, di($C_{1-4}$)alkylamino, cyano, halogen, hydroxy and nitro;

(g) $C_{3-8}$cycloalkyl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, (h) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

Y is one or more optionally present $C_{1-8}$alkyl substituents optionally substituted with one or more substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted;

m is an integer from 2 to 5 which represents the carbon atom number corresponding to the point of attachment for the $R_2$—C(O)— substituent moiety on the anilino ring of formula (Ia); and, n is an integer from 1 to 2.

In an embodiment of the present invention are compounds of formula (Ib):

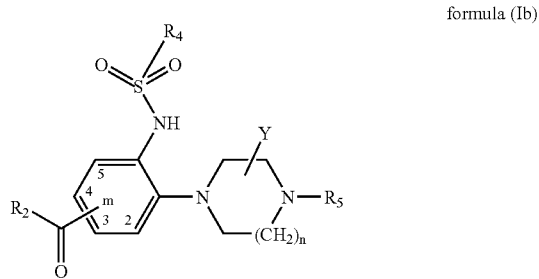

formula (Ib)

and enantiomers, diastereomers and pharmaceutically acceptable salts thereof, wherein:

$R_2$—C(O)— is a substituent moiety having a variable position "m", wherein "m" represents a carbon atom number corresponding to a point of attachment for the $R_2$—C(O)— substituent moiety on the anilino ring of formula (Ib);

$R_2$ is heterocyclyl optionally substituted on a nitrogen atom with $C_{1-8}$alkyl;

R4 is selected from the group consisting of (d) $C_{1-8}$alkyl optionally substituted with one or more substituents independently selected from the group consisting of $C_{1-8}$alkoxy, amino, mono($C_{1-4}$)alkylamino, di($C_{1-4}$)alkylamino, hydroxy, aryl and heteroaryl; and, (e) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

$R_5$ is selected from the group consisting of (f) $C_{1-8}$alkyl optionally substituted with one or more aryl substituents, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro, aryl' and heteroaryl;

wherein said aryl' is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$) alkylamino, di($C_{1-4}$)alkylamino, cyano, halogen, hydroxy and nitro;

(g) $C_{3-8}$cycloalkyl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, (h) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

Y is one or more optionally present $C_{1-8}$alkyl substituents optionally substituted with one or more substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted;

m is an integer from 2 to 5 which represents the carbon atom number corresponding to the point of attachment for the $R_2$—C(O)— substituent moiety on the anilino ring of formula (Ib); and, n is an integer from 1 to 2.

In an embodiment of the present invention are compounds of formula (Ic):

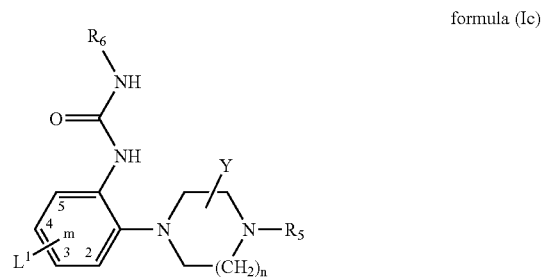

formula (Ic)

and enantiomers, diastereomers and pharmaceutically acceptable salts thereof, wherein:

$L^1$ is a substituent moiety having a variable position "m", wherein "m" represents a carbon atom number corresponding to a point of attachment for the $L^1$ substituent moiety on the anilino ring of formula (Ic);

$L^1$ is selected from the group consisting of $R_{1b}$, $R_{1a}$—SO$_2$— and $R_{1a}$—O(O)C—;

$R_{1a}$, is $C_{1-8}$alkyl optionally substituted with one or more substituents independently selected from the group consisting of $C_{1-8}$alkoxy, amino, mono($C_{1-8}$)alkylamino, di($C_{1-8}$)alkylamino, halogen and hydroxy;

$R_{1b}$ is $C_{1-8}$alkyl optionally substituted with one or more substituents independently selected from the group consisting of amino, mono($C_{1-8}$)alkylamino, di($C_{1-8}$)alkylamino, halogen and hydroxy;

$R_6$ is aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

$R_5$ is selected from the group consisting of (f) $C_{1-8}$alkyl optionally substituted with one or more aryl substituents, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro, aryl' and heteroaryl;

wherein said aryl' is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

(g) $C_{3-8}$cycloalkyl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, (h) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

Y is one or more optionally present $C_{1-8}$alkyl substituents optionally substituted with one or more substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted;

m is an integer from 2 to 5 which represents the carbon atom number corresponding to the point of attachment for the $L^1$ substituent moiety on the anilino ring of formula (Ic); and, n is an integer from 1 to 2.

In an embodiment of the present invention are compounds of formula (Id):

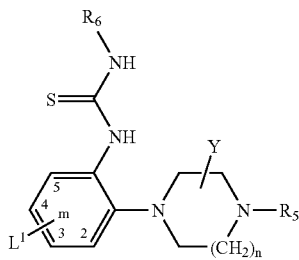

formula (Id)

and enantiomers, diastereomers and pharmaceutically acceptable salts thereof, wherein:

$L^1$ is a substituent moiety having a variable position "m", wherein "m" represents a carbon atom number corresponding to a point of attachment for the $L^1$ substituent moiety on the anilino ring of formula (Id);

$L^1$ is selected from the group consisting of $R_{1b}$, $R_2$—C(O)—, $R_{1a}$—$SO_2$— and $R_{1a}$—O(O)C—;

$R_{1a}$ is $C_{1-8}$alkyl optionally substituted with one or more substituents independently selected from the group consisting of $C_{1-8}$alkoxy, amino, mono($C_{1-8}$)alkylamino, di($C_{1-8}$)alkylamino, halogen and hydroxy;

$R_{1b}$ is $C_{1-8}$alkyl optionally substituted with one or more substituents independently selected from the group consisting of amino, mono($C_{1-8}$)alkylamino, di($C_{1-8}$)alkylamino, halogen and hydroxy;

$R_2$ is heterocyclyl optionally substituted on a nitrogen atom with $C_{1-8}$alkyl;

$R_6$ is aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

$R_5$ is selected from the group consisting of (f) $C_{1-8}$alkyl optionally substituted with one or more aryl substituents, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro, aryl' and heteroaryl;

wherein said aryl' is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-8}$alkyl, and optionally and independently substituted on one or more carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

(g) $C_{3-8}$cycloalkyl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and, (h) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;

Y is one or more optionally present $C_{1-8}$alkyl substituents optionally substituted with one or more substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted;

m is an integer from 2 to 5 which represents the carbon atom number corresponding to the point of attachment for the $L^1$ substituent moiety on the anilino ring of formula (Id); and, n is an integer from 1 to 2.

In an embodiment of the invention are compounds of formula (I), wherein when $L^2$ is $R_3$—C(O)— and $R_3$ is selected from the group consisting of unsubstituted $C_{1-8}$alkyl, substituted aryl, unsubstituted aryl, substituted heteroaryl and unsubstituted heteroaryl, then $L^1$ is $R_2$—C(O).

In an embodiment of the invention are compounds of formula (I), wherein when $L^2$ is $R_3$—C(O)— and $R_3$ is selected from the group consisting of unsubstituted $C_{1-8}$alkyl, substituted aryl, unsubstituted aryl, substituted heteroaryl and unsubstituted heteroaryl, then $R_5$ is $C_{1-8}$alkyl optionally substituted with one or more optionally substituted aryl substituents.

In an embodiment of the invention are compounds of formula (I), wherein when $L^2$ is $R_4$—SO$_2$— and $R_4$ is unsubstituted $C_{1-8}$alkyl, then $L^1$ is $R_2$—C(O), wherein $R_2$ is substituted or unsubstituted heterocyclyl.

In an embodiment of the invention are compounds of formula (I), wherein when $L^2$ is $R_4$—SO$_2$— and $R_4$ is unsubstituted $C_{1-8}$alkyl, then $R_5$ is $C_{1-8}$alkyl optionally substituted with one or more optionally substituted aryl substituents.

In an embodiment of the invention are compounds of formula (I), wherein when $L^1$ is selected from the group consisting of $R_{1b}$ and $R_{1a}$—O(O)C—, then $L^2$ is $R_6$—NHC(O)—, wherein $R_6$ is substituted or unsubstituted aryl.

In an embodiment of the invention are compounds of formula (I), wherein when $L^1$ is selected from the group consisting of $R_{1b}$ and $R_{1a}$—O(O)C—, then $R_5$ is $C_{1-8}$alkyl optionally substituted with one or more optionally substituted aryl substituents.

In an embodiment of the present invention are compounds of formula (I):

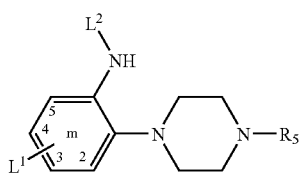

formula (I)

and enantiomers, diastereomers and pharmaceutically acceptable salts thereof, wherein:

$L^1$ is a substituent moiety having a variable position "m", wherein "m" represents a carbon atom number corresponding to a point of attachment for the $L^1$ substituent moiety on the anilino ring of formula (I);

$L^1$ is selected from the group consisting of $R_{1b}$, $R_2$—C(O)—, $R_{1a}$—SO$_2$— and $R_{1a}$—O(O)C—;

$R_{1a}$ is $C_{1-4}$alkyl optionally substituted with one or more substituents independently selected from the group consisting of $C_{1-4}$alkoxy, amino, mono($C_{1-4}$)alkylamino, di($C_{1-4}$)alkylamino, halogen and hydroxy;

$R_{1b}$ is $C_{1-4}$alkyl optionally substituted with one or more substituents independently selected from the group consisting of amino, mono($C_{1-4}$)alkylamino, di($C_{1-4}$)alkylamino, halogen and hydroxy;

$R_2$ is piperazinyl optionally substituted on a nitrogen atom with $C_{1-4}$alkyl;

$L^2$ is selected from the group consisting of $R_3$—C(O)—, $R_4$—SO$_2$—, $R_6$—NHC(S)—and $R_6$—NHC(O)—;

$R_3$ is selected from the group consisting of (a) $C_{1-4}$alkyl optionally substituted with one or two substituents independently selected from the group consisting of $C_{1-8}$alkoxy, amino, mono($C_{1-4}$)alkylamino, di($C_{1-4}$)alkylamino, hydroxy, aryl and heteroaryl;

(b) aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, halogen and hydroxy; and, (c) heteroaryl optionally substituted on a secondary amine atom with $C_{1-4}$alkyl, and optionally and independently substituted on one or two carbon atoms with a substituent selected from the group consisting of $C_{1-4}$alkyl, $C_{1-4}$alkoxy, amino, mono($C_{1-4}$)alkylamino, di($C_{1-4}$)alkylamino, cyano, halogen, hydroxy, nitro and aryl, wherein said aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;

$R_4$ is selected from the group consisting of (d) $C_{1-4}$alkyl optionally substituted with one or two substituents independently selected from the group consisting of $C_{1-4}$alkoxy, amino, mono($C_{1-4}$)alkylamino, di($C_{1-4}$)alkylamino, hydroxy, aryl and heteroaryl; and, (e) aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;

$R_6$ is aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;

$R_5$ is selected from the group consisting of (f) $C_{1-4}$alkyl optionally substituted with one or two aryl substituents, wherein said aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy, nitro, aryl' and heteroaryl;

wherein said aryl' is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro; and, wherein said heteroaryl is optionally substituted on a secondary amine atom with $C_{1-4}$alkyl, and optionally and independently substituted on one or two carbon atoms with a substituent selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;

(g) $C_{3-8}$cycloalkyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro; and, (h) aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro; and, m is an integer from 2 to 5 which represents the carbon atom number corresponding to the point of attachment for the $L^1$ substituent moiety on the anilino ring of formula (I).

In an embodiment of the present invention are compounds of formula (I):

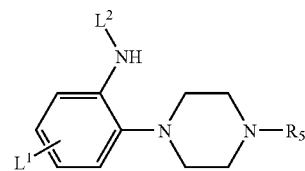

formula (I)

and enantiomers, diastereomers and pharmaceutically acceptable salts thereof, wherein:
$L^1$ is selected from the group consisting of $R_{1b}$, $R_2$—C(O)—, $R_{1a}$—SO$_2$— and $R_{1a}$—O(O)C—;
$R_{1a}$ is $C_{1-4}$alkyl;
$R_{1b}$ is hydroxy($C_{1-4}$)alkyl-;
$R_2$ is piperazinyl optionally substituted on a nitrogen atom with $C_{1-4}$alkyl;
$L^2$ is selected from the group consisting of $R_3$—C(O)—, $R_4$—SO$_2$—, $R_6$—NHC(S)— and $R_6$—NHC(O)—;
$R_3$ is selected from the group consisting of
(a) $C_{1-4}$alkyl;
(b) phenyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, halogen and hydroxy; and,
(c) furyl optionally and independently substituted on one or two carbon atoms with a substituent selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and aryl, wherein said aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;
$R_4$ is selected from the group consisting of
(d) $C_{1-4}$alkyl; and,
(e) phenyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;
$R_6$ is phenyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;
$R_5$ is selected from the group consisting of
$C_{1-4}$alkyl optionally substituted with one or two aryl substituents, wherein aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy, nitro, aryl' and heteroaryl;
(g) $C_{3-8}$cycloalkyl; and,
(h) aryl.

In an embodiment of the present invention are compounds of formula (I):

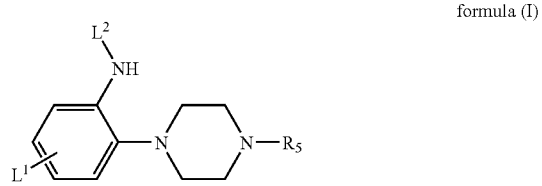

formula (I)

and enantiomers, diastereomers and pharmaceutically acceptable salts thereof, wherein:
$L^1$ is selected from the group consisting of $R_{1b}$, $R_2$—C(O)—, $R_{1a}$—SO$_2$— and $R_{1a}$—O(O)C—;
$R_{1a}$ is $C_{1-4}$alkyl;
$R_{1b}$ is hydroxy($C_{1-4}$)alkyl-;
$R_2$ is piperazinyl optionally substituted on a nitrogen atom with $C_{1-4}$alkyl;
$L^2$ is selected from the group consisting of $R_3$—C(O)—, $R_4$—SO$_2$—, $R_6$—NHC(S)— and $R_6$—NHC(O)—;
$R_3$ is selected from the group consisting of
(a) $C_{1-4}$alkyl;
(b) phenyl optionally substituted with one or two substituents independently selected from the group consisting of $C_{1-4}$alkyl and halogen; and,
(c) furyl optionally and independently substituted on one or two carbon atoms with a substituent selected from the group consisting of $C_{1-4}$alkyl and phenyl;
wherein said phenyl is optionally substituted with one or two substituents independently selected from the group consisting of $C_{1-4}$alkyl and halogen;
$R_4$ is selected from the group consisting of
(d) $C_{1-4}$alkyl; and,
(e) phenyl optionally substituted with one or two substituents independently selected from the group consisting of $C_{1-4}$alkyl and halogen;
$R_6$ is phenyl optionally substituted with one or two substituents independently selected from the group consisting of $C_{1-4}$alkyl, amino, halogen and hydroxy; and,
$R_5$ is selected from the group consisting of
(f) $C_{1-4}$alkyl optionally substituted with one or two phenyl substituents, wherein phenyl is optionally substituted with one or two substituents independently selected from the group consisting of $C_{1-4}$alkyl, amino, halogen and hydroxy.

In an embodiment of the present invention are compounds of formula (I) and formula (Id), wherein $L^1$ is selected from the group consisting of $R_{1b}$, $R_2$—C(O)— and $R_{1a}$—SO$_2$—.

In an embodiment of the present invention are compounds of formula (I) and formula (Id), wherein $L^1$ is selected from the group consisting of $R_2$—C(O)—, $R_{1a}$—SO$_2$— and $R_{1a}$—O(O)C—.

In an embodiment of the present invention are compounds of formula (I) and formula (Id), wherein $L^1$ is selected from the group consisting of $R_{1b}$, $R_{1a}$—SO$_2$— and $R_{1a}$—O(O)C—.

In an embodiment of the present invention are compounds of formula (I) and formula (Id), wherein $L^1$ is selected from the group consisting of $R_{1b}$ and $R_2$—C(O)—.

In an embodiment of the present invention are compounds of formula (I) and formula (Id), wherein $L^1$ is selected from the group consisting of $R_{1a}$—SO$_2$— and $R_{1a}$—O(O)C—.

In an embodiment of the present invention are compounds of formula (I) and formula (Id), wherein $L^1$ is selected from the group consisting of $R_{1b}$ and $R_{1a}$—SO$_2$—.

In an embodiment of the present invention are compounds of formula (I) and formula (Id), wherein $L^1$ is selected from the group consisting of $R_{1b}$ and $R_{1a}$—O(O)C—.

In an embodiment of the present invention are compounds of formula (I) and formula (Id), wherein $L^1$ is $R_{1b}$.

In an embodiment of the present invention are compounds of formula (I) and formula (Id), wherein $L^1$ is $R_2$—C(O)—.

In an embodiment of the present invention are compounds of formula (I) and formula (Id), wherein $L^1$ is $R_{1a}$—SO$_2$—.

In an embodiment of the present invention are compounds of formula (I) and formula (Id), wherein $L^1$ is $R_{1a}$—O(O)C—.

In an embodiment of the present invention are compounds of formula (I), formula (Ic) and formula (Id), wherein $R_{1a}$ is $C_{1-4}$alkyl optionally substituted with one or more substituents independently selected from the group consisting of $C_{1-8}$alkoxy, amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-8}$alkyl optionally substituted with one or more substituents independently selected from the group consisting of amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-8}$alkyl optionally substituted with one or more substituents independently selected from the group consisting of $C_{1-8}$alkoxy, halogen and hydroxy.

In an embodiment of the present invention are compounds of formula (I), formula (Ic) and formula (Id), wherein $R_{1a}$ is $C_{1-8}$alkyl optionally substituted with one or more substituents independently selected from the group consisting of $C_{1-8}$alkoxy, amino, mono($C_{1-8}$)alkylamino, di($C_{1-8}$)alkylamino and hydroxy.

In an embodiment of the present invention are compounds of formula (I), formula (Ic) and formula (Id), wherein $R_{1a}$ is $C_{1-8}$alkyl optionally substituted with one or more substituents independently selected from the group consisting of $C_{1-8}$alkoxy, amino, mono($C_{1-8}$)alkylamino, di($C_{1-8}$)alkylamino and halogen.

In an embodiment of the present invention are compounds of formula (I), formula (Ic) and formula (Id), wherein $R_{1a}$ is $C_{1-4}$alkyl optionally substituted with one or more substituents independently selected from the group consisting of amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-4}$alkyl optionally substituted with one or more substituents independently selected from the group consisting of $C_{1-8}$alkoxy, halogen and hydroxy.

In an embodiment of the present invention are compounds of formula (I), formula (Ic) and formula (Id), wherein $R_{1a}$ is $C_{1-4}$alkyl optionally substituted with one or more substituents independently selected from the group consisting of $C_{1-8}$alkoxy, amino, mono($C_{1-8}$)alkylamino, di($C_{1-8}$)alkylamino and hydroxy.

In an embodiment of the present invention are compounds of formula (I), formula (Ic) and formula (Id), wherein $R_{1a}$ is $C_{1-4}$alkyl optionally substituted with one or more substituents independently selected from the group consisting of $C_{1-8}$alkoxy, amino, mono($C_{1-8}$)alkylamino, di($C_{1-8}$)alkylamino and halogen.

In an embodiment of the present invention are compounds of formula (I), formula (Ic) and formula (Id), wherein $R_{1a}$ is $C_{1-8}$alkyl.

In an embodiment of the present invention are compounds of formula (I), formula (Ic) and formula (Id), wherein $R_{1a}$ is $C_{1-4}$alkyl.

In an embodiment of the present invention are compounds of formula (I), formula (Ic) and formula (Id), wherein $R_{1b}$ is $C_{1-8}$alkyl optionally substituted with one or more substituents independently selected from the group consisting of amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-4}$alkyl optionally substituted with one or two substituents independently selected from the group consisting of $C_{1-8}$alkoxy, amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-8}$alkyl optionally substituted with one or two substituents independently selected from the group consisting of amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-8}$alkyl optionally substituted with one or two substituents independently selected from the group consisting of $C_{1-8}$alkoxy, halogen and hydroxy.

In an embodiment of the present invention are compounds of formula (I), formula (Ic) and formula (Id), wherein $R_{1a}$ is $C_{1-8}$alkyl optionally substituted with one or two substituents independently selected from the group consisting of $C_{1-8}$alkoxy, amino, mono($C_{1-8}$)alkylamino, di($C_{1-8}$)alkylamino and hydroxy.

In an embodiment of the present invention are compounds of formula (I), formula (Ic) and formula (Id), wherein $R_{1a}$ is $C_{1-8}$alkyl optionally substituted with one or two substituents independently selected from the group consisting of $C_{1-8}$alkoxy, amino, mono($C_{1-8}$)alkylamino, di($C_{1-8}$)alkylamino and halogen.

In an embodiment of the present invention are compounds of formula (I), formula (Ic) and formula (Id), wherein $R_{1a}$ is $C_{1-4}$alkyl optionally substituted with one or two substituents independently selected from the group consisting of amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-4}$alkyl optionally substituted with one or two substituents independently selected from the group consisting of $C_{1-8}$alkoxy, halogen and hydroxy.

In an embodiment of the present invention are compounds of formula (I), formula (Ic) and formula (Id), wherein $R_{1a}$ is $C_{1-4}$alkyl optionally substituted with one or two substituents independently selected from the group consisting of $C_{1-8}$alkoxy, amino, mono($C_{1-8}$)alkylamino, di($C_{1-8}$)alkylamino and hydroxy.

In an embodiment of the present invention are compounds of formula (I), formula (Ic) and formula (Id), wherein $R_{1a}$ is $C_{1-4}$alkyl optionally substituted with one or two substituents independently selected from the group consisting of $C_{1-8}$alkoxy, amino, mono($C_{1-8}$)alkylamino, di($C_{1-8}$)alkylamino and halogen.

In an embodiment of the present invention are compounds of formula (I), formula (Ic) and formula (Id), wherein $R_{1a}$ is $C_{1-4}$alkyl optionally substituted with one substituent selected from the group consisting of $C_{1-8}$alkoxy, amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-8}$alkyl optionally substituted with one substituent selected from the group consisting of amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-8}$alkyl optionally substituted with one substituent selected from the group consisting of $C_{1-8}$alkoxy, halogen and hydroxy.

In an embodiment of the present invention are compounds of formula (I), formula (Ic) and formula (Id), wherein $R_{1a}$ is $C_{1-8}$alkyl optionally substituted with one substituent selected from the group consisting of $C_{1-8}$alkoxy, amino, mono($C_{1-8}$)alkylamino, di($C_{1-8}$)alkylamino and hydroxy.

In an embodiment of the present invention are compounds of formula (I), formula (Ic) and formula (Id), wherein $R_{1a}$ is $C_{1-8}$alkyl optionally substituted with one substituent selected from the group consisting of $C_{1-8}$alkoxy, amino, mono($C_{1-8}$)alkylamino, di($C_{1-8}$)alkylamino and halogen.

In an embodiment of the present invention are compounds of formula (I), formula (Ic) and formula (Id), wherein $R_{1a}$ is $C_{1-4}$alkyl optionally substituted with one substituent selected from the group consisting of amino, mono($C_{1-8}$)alkylamino, di($C_{1-8}$)alkylamino, halogen and hydroxy.

In an embodiment of the present invention are compounds of formula (I), formula (Ic) and formula (Id), wherein $R_{1a}$ is $C_{1-4}$alkyl optionally substituted with one substituent selected from the group consisting of $C_{1-8}$alkoxy, halogen and hydroxy.

In an embodiment of the present invention are compounds of formula (I), formula (Ic) and formula (Id), wherein $R_{1a}$ is $C_{1-4}$alkyl optionally substituted with one substituent selected from the group consisting of $C_{1-8}$alkoxy, amino, mono($C_{1-8}$)alkylamino, di($C_{1-8}$)alkylamino and hydroxy.

In an embodiment of the present invention are compounds of formula (I), formula (Ic) and formula (Id), wherein $R_{1a}$ is $C_{1-4}$alkyl optionally substituted with one substituent selected from the group consisting of $C_{1-8}$alkoxy, amino, mono($C_{1-8}$)alkylamino, di($C_{1-8}$)alkylamino and halogen.

In an embodiment of the present invention are compounds of formulae (I), (Ic) and (Id), wherein $R_{1b}$ is $C_{1-4}$alkyl optionally substituted with one or more substituents independently selected from the group consisting of amino, mono($C_{1-8}$)alkylamino, di($C_{1-8}$)alkylamino, halogen and hydroxy.

In an embodiment of the present invention are compounds of formulae (I), (Ic) and (Id), wherein $R_{1b}$ is $C_{1-8}$alkyl optionally substituted with one or more substituents independently selected from the group consisting of amino, mono($C_{1-8}$)alkylamino and di($C_{1-8}$)alkylamino.

In an embodiment of the present invention are compounds of formulae (I), (Ic) and (Id), wherein $R_{1b}$ is $C_{1-8}$alkyl optionally substituted with one or more substituents independently selected from the group consisting of amino, mono($C_{1-8}$)alkylamino, di($C_{1-8}$)alkylamino and halogen.

In an embodiment of the present invention are compounds of formulae (I), (Ic) and (Id), wherein $R_{1b}$ is $C_{1-8}$alkyl optionally substituted with one or more substituents independently selected from the group consisting of amino, mono($C_{1-8}$)alkylamino, di($C_{1-8}$)alkylamino and hydroxy.

In an embodiment of the present invention are compounds of formulae (I), (Ic) and (Id), wherein $R_{1b}$ is $C_{1-4}$alkyl optionally substituted with one or more substituents independently selected from the group consisting of amino, mono($C_{1-8}$)alkylamino, di($C_{1-8}$)alkylamino and halogen.

In an embodiment of the present invention are compounds of formulae (I), (Ic) and (Id), wherein $R_{1b}$ is $C_{1-4}$alkyl optionally substituted with one or more substituents independently selected from the group consisting of amino, mono($C_{1-8}$)alkylamino, di($C_{1-8}$)alkylamino and hydroxy.

In an embodiment of the present invention are compounds of formulae (I), (Ic) and (Id), wherein $R_{1b}$ is $C_{1-4}$alkyl optionally substituted with one or two substituents independently selected from the group consisting of amino, mono($C_{1-8}$)alkylamino, di($C_{1-8}$)alkylamino, halogen and hydroxy.

In an embodiment of the present invention are compounds of formulae (I), (Ic) and (Id), wherein $R_{1b}$ is $C_{1-8}$alkyl optionally substituted with one or two substituents independently selected from the group consisting of amino, mono($C_{1-8}$)alkylamino and di($C_{1-8}$)alkylamino.

In an embodiment of the present invention are compounds of formulae (I), (Ic) and (Id), wherein $R_{1b}$ is $C_{1-8}$alkyl optionally substituted with one or two substituents independently selected from the group consisting of amino, mono($C_{1-8}$)alkylamino, di($C_{1-8}$)alkylamino and halogen.

In an embodiment of the present invention are compounds of formulae (I), (Ic) and (Id), wherein $R_{1b}$ is $C_{1-8}$alkyl optionally substituted with one or two substituents independently selected from the group consisting of amino, mono($C_{1-8}$)alkylamino, di($C_{1-8}$)alkylamino and hydroxy.

In an embodiment of the present invention are compounds of formulae (I), (Ic) and (Id), wherein $R_{1b}$ is $C_{1-4}$alkyl optionally substituted with one or two substituents independently selected from the group consisting of amino, mono($C_{1-8}$)alkylamino, di($C_{1-8}$)alkylamino and halogen.

In an embodiment of the present invention are compounds of formulae (I), (Ic) and (Id), wherein $R_{1b}$ is $C_{1-4}$alkyl optionally substituted with one or two substituents independently selected from the group consisting of amino, mono($C_{1-8}$)alkylamino, di($C_{1-8}$)alkylamino and hydroxy.

In an embodiment of the present invention are compounds of formulae (I), (Ic) and (Id), wherein $R_{1b}$ is $C_{1-4}$alkyl optionally substituted with one substituent selected from the group consisting of amino, mono($C_{1-8}$)alkylamino, di($C_{1-8}$)alkylamino, halogen and hydroxy.

In an embodiment of the present invention are compounds of formulae (I), (Ic) and (Id), wherein $R_{1b}$ is $C_{1-4}$alkyl optionally substituted with one substituent selected from the group consisting of amino, mono($C_{1-8}$)alkylamino and di($C_{1-8}$)alkylamino.

In an embodiment of the present invention are compounds of formulae (I), (Ic) and (Id), wherein $R_{1b}$ is $C_{1-4}$alkyl optionally substituted with halogen.

In an embodiment of the present invention are compounds of formulae (I), (Ic) and (Id), wherein $R_{1b}$ is $C_{1-4}$alkyl optionally substituted with hydroxy.

In an embodiment of the present invention are compounds of formulae (I), (Ic) and (Id), wherein $R_{1b}$ is hydroxy($C_{1-4}$)alkyl-.

In an embodiment of the present invention are compounds of formulae (I), (Ia), (Ib) and (Id), wherein $R_2$ is piperazinyl optionally substituted on a nitrogen atom with $C_{1-8}$alkyl.

In an embodiment of the present invention are compounds of formulae (I), (Ia), (Ib) and (Id), wherein $R_2$ is piperazinyl optionally substituted on a nitrogen atom with $C_{1-4}$alkyl.

In an embodiment of the present invention are compounds of formulae (I), (Ia), (Ib) and (Id), wherein $R_2$ is piperazinyl.

In an embodiment of the present invention are compounds of formula (I), wherein $L^2$ is $R_3$—C(O)—.

In an embodiment of the present invention are compounds of formula (I), wherein $L^2$ is $R_4$—SO$_2$—.

In an embodiment of the present invention are compounds of formula (I), wherein $L^2$ is $R_6$—NHC(O)—.

In an embodiment of the present invention are compounds of formula (I), wherein $L^2$ is $R_6$—NHC(S)—.

In an embodiment of the present invention are compounds of formulae (I) and (Ia), wherein $R_3$ is selected from the group consisting of (a) $C_{1-8}$alkyl optionally substituted with one or more substituents independently selected from the group consisting of $C_{1-8}$alkoxy, amino, mono($C_{1-4}$)alkylamino, di($C_{1-4}$)alkylamino, hydroxy, aryl and heteroaryl;
wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and,
wherein said heteroaryl is optionally substituted on a secondary amine atom with $C_{1-8}$alkyl, and optionally and independently substituted on one or two carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;
(b) aryl optionally substituted with one or more substituents independently selected from the group consisting of $C_{1-8}$alkyl, $C_{1-18}$alkoxy, amino, mono($C_{1-4}$)alkylamino, di($C_{1-4}$)alkylamino, cyano, halogen, hydroxy and nitro; and,
(c) heteroaryl optionally substituted on a secondary amine atom with $C_{1-8}$alkyl, and optionally and independently substituted on one or two carbon atoms with a substituent selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro and aryl, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro.

In an embodiment of the present invention are compounds of formulae (I) and (Ia), wherein $R_3$ is selected from the group consisting of
(a) $C_{1-4}$alkyl;
(b) aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, halogen and hydroxy; and,
(c) heteroaryl optionally substituted on a secondary amine atom with $C_{1-4}$alkyl, and optionally and independently substituted on one or two carbon atoms with a substituent selected from the group consisting of $C_{1-4}$alkyl, $C_{1-4}$alkoxy, amino, mono($C_{1-4}$)alkylamino, di($C_{1-4}$)alkylamino, cyano, halogen, hydroxy, nitro and aryl, wherein said aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro.

In an embodiment of the present invention are compounds of formulae (I) and (Ia), wherein $R_3$ is selected from the group consisting of
(a) $C_{1-4}$alkyl;
(b) phenyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, halogen and hydroxy; and,
(c) furyl optionally and independently substituted on one or two carbon atoms with a substituent selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and aryl, wherein said aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro.

In an embodiment of the present invention are compounds of formulae (I) and (Ia), wherein $R_3$ is selected from the group consisting of
(a) $C_{1-4}$alkyl;
(b) phenyl optionally substituted with one or two substituents independently selected from the group consisting of $C_{1-4}$alkyl and halogen; and,
(c) furyl optionally and independently substituted on one or two carbon atoms with a substituent selected from the group consisting of $C_{1-4}$alkyl and phenyl;
wherein said phenyl is optionally substituted with one or two substituents independently selected from the group consisting of $C_{1-4}$alkyl and halogen.

In an embodiment of the present invention are compounds of formulae (I) and (Ib), wherein $R_4$ is selected from the group consisting of
(d) $C_{1-8}$alkyl optionally substituted with one or more substituents independently selected from the group consisting of $C_{1-8}$alkoxy, amino, mono($C_{1-4}$)alkylamino, di($C_{1-4}$)alkylamino, hydroxy, aryl and heteroaryl; and,
(e) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro.

In an embodiment of the present invention are compounds of formulae (I) and (Ib), wherein $R_4$ is selected from the group consisting of
(d) $C_{1-4}$alkyl optionally substituted with one or two substituents independently selected from the group consisting of $C_{1-4}$alkoxy, amino, mono($C_{1-4}$)alkylamino, di($C_{1-4}$)alkylamino, hydroxy, aryl and heteroaryl; and,
(e) aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro.

In an embodiment of the present invention are compounds of formulae (I) and (Ib), wherein $R_4$ is selected from the group consisting of
(d) $C_{1-4}$alkyl; and,
(e) phenyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro.

In an embodiment of the present invention are compounds of formulae (I) and (Ib), wherein $R_4$ is selected from the group consisting of
(d) $C_{1-4}$alkyl; and,
(e) phenyl optionally substituted with one or two substituents independently selected from the group consisting of $C_{1-4}$alkyl and halogen.

In an embodiment of the present invention are compounds of formulae (I), (Ic) and (Id), wherein $R_6$ is aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro.

In an embodiment of the present invention are compounds of formulae (I), (Ic) and (Id), wherein $R_6$ is aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro.

In an embodiment of the present invention are compounds of formulae (I), (Ic) and (Id), wherein $R_6$ is phenyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro.

In an embodiment of the present invention are compounds of formulae (I), (Ic) and (Id), wherein $R_6$ is phenyl optionally substituted with one or two substituents independently selected from the group consisting of $C_{1-4}$alkyl, amino, halogen and hydroxy.

In an embodiment of the present invention are compounds of formulae (I), (Ia), (Ib), (Ic) and (Id), wherein $R_5$ is selected from the group consisting of
(f) $C_{1-8}$alkyl optionally substituted with one or more aryl substituents, wherein said aryl is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy, nitro, aryl' and heteroaryl;
  wherein said aryl' is optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and,
  wherein said heteroaryl is optionally substituted on a secondary amine atom with $C_{1-8}$alkyl, and optionally and independently substituted on a carbon atom with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro;
(g) $C_{3-8}$cycloalkyl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro; and,
(h) aryl optionally substituted with one or more substituents independently selected from the group consisting of $C_{1-8}$alkyl, $C_{1-8}$alkoxy, amino, mono($C_{1-4}$)alkylamino, di($C_{1-4}$)alkylamino, cyano, halogen, hydroxy and nitro.

In a preferred embodiment of the present invention are compounds of formulae (I), (Ia), (Ib), (Ic) and (Id), wherein $R_5$ is selected from the group consisting of
(f) $C_{1-4}$alkyl optionally substituted with one or two aryl substituents, wherein said aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy, nitro, aryl' and heteroaryl;
  wherein said aryl' is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro; and,
  wherein said heteroaryl is optionally substituted on a secondary amine atom with $C_{1-4}$alkyl, and optionally and independently substituted on one or two carbon atoms with a substituent selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;
(g) $C_{3-8}$cycloalkyl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro; and,
(h) aryl optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro.

In an embodiment of the present invention are compounds of formulae (I), (Ia), (Ib), (Ic) and (Id), wherein $R_5$ is selected from the group consisting of
(f) $C_{1-4}$alkyl optionally substituted with one or two aryl substituents, wherein aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy, nitro, aryl' and heteroaryl;
(g) $C_{3-8}$cycloalkyl; and,
(h) aryl.

In an embodiment of the present invention are compounds of formulae (I), (Ia), (Ib), (Ic) and (Id), wherein $R_5$ is selected from the group consisting of
(f) $C_{1-4}$alkyl optionally substituted with one or two aryl substituents, wherein aryl is optionally substituted with one or two substituents independently selected from the group consisting of $C_{1-4}$alkyl, $C_{1-4}$alkoxy, amino, mono($C_{1-4}$)alkylamino, di($C_{1-4}$)alkylamino, cyano, halogen, hydroxy and nitro;
(g) $C_{3-8}$cycloalkyl; and,
(h) aryl.

In an embodiment of the present invention are compounds of formulae (I), (Ia), (Ib), (Ic) and (Id), wherein $R_5$ is selected from the group consisting of
(f) $C_{1-4}$alkyl optionally substituted with one or two phenyl substituents, wherein phenyl is optionally substituted with one or two substituents independently selected from the group consisting of $C_{1-4}$alkyl, amino, halogen and hydroxy.

In an embodiment of the present invention are compounds of formulae (I), (Ia), (Ib), (Ic) and (Id), wherein Y is one or two optionally present $C_{1-8}$alkyl substituents optionally substituted with one or two substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted.

In an embodiment of the present invention are compounds of formulae (I), (Ia), (Ib), (Ic) and (Id), wherein Y is one or two optionally present $C_{1-4}$alkyl substituents optionally substituted with one or two substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted.

In an embodiment of the present invention are compounds of formulae (I), (Ia), (Ib), (Ic) and (Id), wherein Y is one or two optionally present $C_{1-4}$alkyl substituents optionally substituted with one or two substituents independently selected from the group consisting of amino, mono($C_{1-4}$)alkylamino, di($C_{1-4}$)alkylamino, cyano, halogen, hydroxy, nitro, $C_{3-8}$cycloalkyl, aryl and heteroaryl, wherein said $C_{3-8}$cycloalkyl, aryl and heteroaryl are optionally further substituted.

In an embodiment of the present invention are compounds of formulae (I), (Ia), (Ib), (Ic) and (Id), wherein Y is one or two optionally present $C_{1-4}$alkyl substituents optionally substituted with one or two substituents independently selected from the group consisting of amino, mono($C_{1-4}$)alkylamino and di($C_{1-4}$)alkylamino.

In an embodiment of the present invention are compounds of formulae (I), (Ia), (Ib), (Ic) and (Id), wherein Y is one or two optionally present $C_{1-4}$alkyl substituents optionally substituted with one or two substituents independently selected from the group consisting of cyano, halogen, hydroxy, nitro, $C_{3-8}$cycloalkyl, aryl and heteroaryl, wherein said $C_{3-8}$cycloalkyl, aryl and heteroaryl are optionally further substituted.

In an embodiment of the present invention are compounds of formulae (I), (Ia), (Ib), (Ic) and (Id), wherein Y is one or two optionally present $C_{1-4}$alkyl substituents optionally substituted with one or two substituents independently selected from the group consisting of halogen, hydroxy, $C_{3-8}$cycloalkyl, aryl and heteroaryl, wherein said $C_{3-8}$cycloalkyl, aryl and heteroaryl are optionally further substituted.

In an embodiment of the present invention are compounds of formulae (I), (Ia), (Ib), (Ic) and (Id), wherein Y is one or two optionally present $C_{1-4}$alkyl substituents optionally substituted with one or two substituents independently selected from the group consisting of $C_{3-8}$cycloalkyl, aryl and heteroaryl, wherein said $C_{3-8}$cycloalkyl, aryl and heteroaryl are optionally further substituted.

In an embodiment of the present invention are compounds of formulae (I), (Ia), (Ib), (Ic) and (Id), wherein Y is absent.

Embodiments of the present invention include a compound of formula (I), wherein m is 5, as shown below:

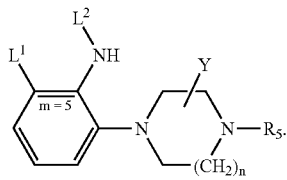

Further, embodiments of the present invention include a compound of formula (I), wherein m is 4 as shown below:

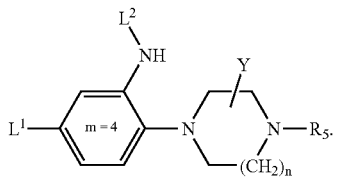

Further, embodiments of the present invention include a compound of formula (I), wherein m is 3 as shown below:

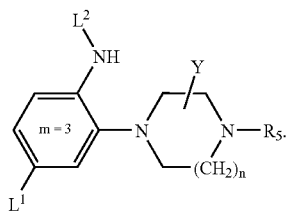

Further, embodiments of the present invention include a compound of formula (I), wherein m is 2 as shown below:

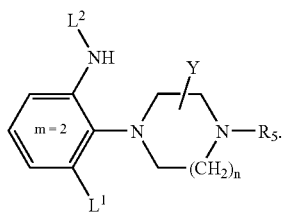

Further embodiments of the present invention include a compound of formulae Ia), (Ib), (Ic) and (Id):

wherein m is 5; or wherein m is 2; or, preferably, wherein m is 3; or, preferably, wherein m is 4.

Embodiments of the present invention include a compound of formula (I), (Ia), (Ib), (Ic) and (Id), wherein n is 1.

In an embodiment of the present invention are compounds of formula (I)

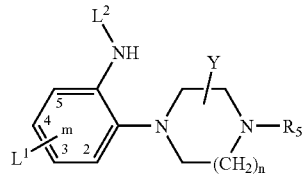

formula (I)

and enantiomers, diastereomers and pharmaceutically acceptable salts thereof, wherein n is 1, m is 4, Y is absent and $L^1$, $L^2$, and $R_5$ are dependently selected from the group consisting of:

| Cpd | $L^1$ | $L^2$ | $R_5$ |
|---|---|---|---|
| 1 | —C(O)-piperazin-1-yl | —C(O)-(4-$CH_3$-Ph) | —CH(Ph)$_2$, |
| 2 | —C(O)-piperazin-1-yl | —C(O)-[2-$CH_3$-5-(4-Cl-Ph)-3-furyl] | —CH(Ph)$_2$, |
| 3 | —C(O)-piperazin-1-yl | —C(O)-2-furyl | —CH(Ph)$_2$, |
| 4 | —C(O)-piperazin-1-yl | —C(O)—$CH_2CH_3$ | —CH(Ph)$_2$, |
| 5 | —C(O)-piperazin-1-yl | —$SO_2$-(4-$CH_3$-Ph) | —CH(Ph)$_2$, |
| 6 | —C(O)-piperazin-1-yl | —$SO_2$-(4-Cl-Ph) | —CH(Ph)$_2$, |
| 7 | —C(O)-piperazin-1-yl | —$SO_2$—$(CH_2)_3CH_3$ | —CH(Ph)$_2$, |
| 8 | —C(O)-piperazin-1-yl | —$SO_2$—$CH_3$ | —CH(Ph)$_2$, |
| 9 | —$SO_2$—$CH_3$ | —C(O)—NH-Ph | —CH(Ph)$_2$, |
| 10 | —$CH_2OH$ | —C(O)—NH-Ph | —CH(4-F-Ph)$_2$, and |
| 11 | —C(O)O—$CH_3$ | —C(O)—NH-Ph | —CH(4-F-Ph)$_2$. |

Chemical Definitions & Nomenclature

As used herein, the following terms are intended to have the following meanings (additional definitions are provided throughout the Specification):

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-3}$ denotes a radical containing 1, 2 or 3 carbon atoms.

The term "alkyl," whether used alone or as part of a substituent group, refers to a saturated branched, or straight chain monovalent hydrocarbon radical derived by the removal of one hydrogen atom from a single carbon atom of a parent alkyl, alkene or alkyne. Typical alkyl groups include, but are not limited to, methyl, ethyl or propyl and the like and can be referred to as methanyl, ethanyl, propanyl (such as propan-1-yl, propan-2-yl, etc.) or butanyl (such as butan-1-yl, butan-2-yl, 2-methyl-propan-1-yl, 2-methyl-propan-2-yl, etc.) and the like. Where specific levels of unsaturation are intended, the nomenclature "alkenyl" and/or "alkynyl" is used, as defined below. In preferred embodiments, alkyl is ($C_{1-8}$)alkyl.

The term "alkenyl," whether used alone or as part of a substituent group, refers to an unsaturated branched or straight chain monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl, propenyl, butenyl and the like (such as prop-1-en-1-yl, prop-1-en-2-yl, prop-2-en-1-yl, prop-2-en-2-yl, but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl and the like). In preferred embodiments, alkenyl is ($C_{2-8}$)alkenyl.

The term "alkynyl," whether used alone or as part of a substituent group, refers to an unsaturated branched, or straight chain monovalent hydrocarbon radical having at least one carbon-carbon triple bond derived by the removal of one hydrogen atom from a single carbon atom of a parent alkyne. Typical alkynyl groups include, but are not limited to, ethynyl, propynyl, butynyl and the like (such as prop-1-yn-1-yl, prop-2-yn-1-yl, but-1-yn-1-yl, but-1-yn-3-yl, but-3-yn-1-yl and the like). In preferred embodiments, alkynyl is $(C_{2-8})$alkynyl.

The term "alkoxy" refers to a saturated or unsaturated, branched or straight chain monovalent hydrocarbon alcohol radical derived by the removal of the hydrogen atom from the hydroxide oxygen of an alcohol of a parent alkyl, alkene or alkyne. Where specific levels of saturation are intended, the nomenclature "alkoxy", "alkenyloxy" and/or "alkynyloxy" is used consistent with the definitions of alkyl, alkenyl and alkynyl. In preferred embodiments, the alkoxy groups are $(C_{1-8})$alkoxy groups.

The term "cycloalkyl" refers to saturated moncyclic hydrocarbon rings of from 3 to 20 carbon atom members (preferably, from 3 to 14 carbon atom members; more preferably, from 3 to 10 carbon atoms). Examples of cycloalkyl rings include, and are not limited to, cyclopropyl, cyclobutyl, cyclopentyl, cyclohexyl, cycloheptyl, adamantyl, indanyl and the like. Where specific levels of saturation are intended, the terms "cycloalkyl" and "cycloalkenyl" are used consistent with the definition of alkyl and alkenyl.

The term "heterocyclyl" refers to a saturated monocyclic alkyl radical of from 5 to 9 ring members in which one or more ring carbon atoms are independently replaced with a heteroatom. Preferred heteroatoms to replace the carbon atom(s) are N, O or S. In preferred embodiments, 1, 2, 3 or 4 members of the ring are a nitrogen atom, or 0, 1, 2 or 3 members of the ring are nitrogen atoms and 1 member is an oxygen or sulfur atom. Examples of heterocyclyl rings include, and are not limited to, pyrrolidinyl, dioxolanyl, imidazolidinyl, pyrazolidinyl, tetrazolidinyl, piperidinyl, dioxanyl, morpholinyl, 1,4-dithianyl, thiomorpholinyl, piperazinyl, hexahydro-1,4-diazepinyl and the like.

The term "aryl" refers to a monovalent aromatic hydrocarbon radical derived by the removal of one hydrogen atom from a single carbon atom of a parent aromatic ring system (The term "parent aromatic ring system" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, naphthalene, indane, indene, phenalene, etc.). Preferred aryl embodiments are derived from unsaturated or partially saturated monocyclic rings of 6 carbon members or from unsaturated or partially saturated fused ring systems of from 10 to 20 carbon members. Examples of aryl rings include, and are not limited to, phenyl, naphthalenyl, fluorenyl, indenyl, anthracenyl and the like.

The term "heteroaryl" refers to a monovalent heteroaromatic radical derived by the removal of one hydrogen atom from a single atom of a parent heteroaromatic ring system (The term "parent heteroaromatic ring system" refers to a parent aromatic ring system in which one or more carbon atoms are each independently replaced with a heteroatom. Preferred heteroatoms to replace the carbon atom(s) are N, P, O or S. Specifically included within the definition of "parent heteroaromatic ring systems" are fused ring systems in which one or more rings are heteroaromatic and one or more rings are saturated or unsaturated, such as, for example, indazole, indole, etc. Preferred heteroaryl embodiments include unsaturated or partially saturated monocyclic rings of from 5 to 9 ring members wherein the ring members consist of carbon atoms and at least one heteroatom. In other preferred embodiments, 1, 2, 3 or 4 members are nitrogen atoms or 0, 1, 2 or 3 members are nitrogen atoms and 1 member is an oxygen or sulfur atom. In other preferred embodiments, when allowed, up to two adjacent ring members are heteroatoms. Examples of heteroaryl rings include, and are not limited to, furyl, thienyl, pyrrolyl (including 2H-pyrrole, 2-pyrrolinyl or 3-pyrrolinyl), oxazolyl, thiazolyl, imidazolyl (including 2-imidazolinyl), pyrazolyl (including 2-pyrazolinyl), isoxazolyl, isothiazolyl, oxadiazolyl, triazolyl, thiadiazolyl, pyridinyl, pyridazinyl, pyrimidinyl, pyrazinyl and the like.

"Fused ring systems" include systems fused at adjacent ring atoms, those fused at a single ring atom and those fused at nonadjacent ring atoms. Preferably, those fused on adjacent ring atoms form bicyclic or polycyclic ring systems, those fused on a single ring atom form spiro moieties and those fused on nonadjacent ring atoms form bridged ring systems. The types and amount of rings formed may be limited by available ring valences, starting materials or synthetic methods. However, all fused ring systems are intended to be included in the scope of the present compounds and associated synthetic methods.

Examples of fused cycloalkyl rings include adamantanyl, indanyl and the like. Examples of fused aryl rings include naphthalenyl, fluorenyl, indenyl, anthracenyl and the like. Examples of fused heterocyclyl rings include 1,3-benzodioxolyl, 2,3-dihydro-1,4-benzodioxinyl and the like. Examples of fused heteroaryl rings include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl, quinazolinyl and the like.

The term "point of attachment," refers to a carbon atom within a radical which acts as the point of attachment for the radical to a core molecule; e.g., for a molecule C(O)—R, wherein a radical R is selected from a hydrogen or $C_{1-8}$alkyl, the $C_{1-8}$alkyl radical is attached to the molecule C(O)— by any carbon atom within the $C_{1-8}$alkyl chain. Accordingly, a variety of structures known to those with skill in the art are possible, such as $C(O)CH_2CH_3$ or $C(O)CH(CH_3)_2$.

The terms "secondary amine member" or "secondary amine atom" refer to a moiety of the formula $R_a$—NH—$R_b$, wherein the NH portion of the formula $R_a$—NH—$R_b$ represents the secondary amine atom and, wherein $R_a$ and $R_b$ represent either identical or different adjacent atoms. The moiety is present in a heterocyclyl or heteroaryl ring system radical such as pyrrolyl, pyrrolinyl, pyrrolidinyl, imidazolyl, imidazolinyl, imidazolidinyl and the like. The secondary amine atom forms the point of attachment to a core molecule for the ring system radical in which it is present or the point of attachment for a substituent to the radical.

Where a radical is "substituted," the term "substituted" refers to the independent replacement of one or more hydrogen atoms within the radical with that amount of substitutents allowed by available valences. The term "independent(ly)" means that when a group or radical is substituted with more than one substituent that the substituents may be the same or different. Substitution is not limited to a terminal atom, but may occur within the radical or on a terminal atom.

The term "dependently substituted" means that the sub-situents are specified in an indicated combination of structure variables.

Where a radical or group of radicals is refered to as being "optionally present," the term "optionally present" refers to the replacement of one or more hydrogen atoms at a point of attachment on a core structure with that amount of radicals allowed by available valences; wherein, the point of attachment is otherwise saturated or aromatic when the radical(s) is (are) not present.

In general, IUPAC nomenclature rules are used throughout this disclosure. Nomenclature for radical substituents is derived by first indicating the functionality having the point of attachment with a hyphen, followed by the adjacent functionality toward the terminal portion of the side chain, as in:

—($C_{1-6}$)alkyl-C(O)NH—($C_{1-6}$)alkyl-Ph or by describing the terminal portion of the side chain first, followed by the adjacent functionality toward the point of attachment, as in:

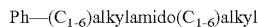

Ph—($C_{1-6}$)alkylamido($C_{1-6}$)alkyl either of which refers to a radical of the formula:

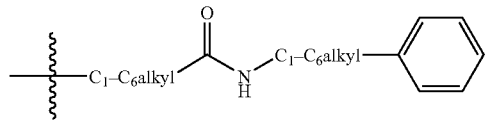

Compounds exemplified in the present invention were named according to nomenclature well known in the art, either using Autonom (brand of nomenclature software provided in the ChemDraw Ultra® office suite marketed by CambridgeSoft.com) or using ACD/Index Name™ (brand of commercial nomenclature software marketed by Advanced Chemistry Development, Inc., Toronto, Ontario).

Pharmaceutical Preparations & Methods of Use

The compounds of the present invention may also be present in the form of pharmaceutically acceptable salts. For use in medicine, the salts of the compounds of this invention refer to non-toxic "pharmaceutically acceptable salts." FDA approved pharmaceutically acceptable salt forms (*Ref. International J. Pharm.* 1986, 33, 201-217; *J. Pharm. Sci.*, 1977, Jan, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, SEH, sodium, sodium carbonate, sodium-2-ethylhexanoate, sodium hydroxide, triethanolamine (TEA) or zinc.

The present invention includes within its scope prodrugs of the compounds of this invention. In general, such prodrugs will be functional derivatives of the compounds, which are readily convertible in vivo into an active compound. Thus, in the methods of treatment of the present invention, the term "administering" shall encompass the treatment of the various disorders described with the compound specifically disclosed or a compound, or prodrug thereof, which would be obviously included within the scope of the invention although not specifically disclosed for certain of the instant compounds. Conventional procedures for the selection and preparation of suitable prodrug derivatives are described, for example, in "*Design of Prodrugs*", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such stereoisomers and mixtures thereof are encompassed within the scope of the present invention. The terms "S" and "R," when used herein for indicating stereoisomer configuration, are as defined in the literature (IUPAC Recommendations for Fundamental Stereochemistry (Section E), *Pure Appl. Chem.*, 1976, 45:13-30).

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M.

Wuts, *Protective Groups in Organic Synthesis*, John Wiley & Sons, 1991. The protecting groups may be removed at a convenient subsequent stage using methods known in the art.

Embodiments of the present invention comprise the use of compounds that are phospholipase inhibitors for treating or ameliorating an inflammatory disorder. The term phospholipase refers to any one of the subtypes of the class of phospholipases activated following binding of a ligand to its cell surface receptor, such as phospholipase C, phospholipase C-β1 or phospholipase C-β2.

An embodiment of the present invention comprises the use of compounds that are selective phospholipase inhibitors for treating or ameliorating an inflammatory disorder. The usefulness of a compound of formula (I) as a phospholipase inhibitor can be determined according to the methods disclosed herein and the scope of such usefulness includes use in a plurality of inflammatory disorders.

An embodiment of the present invention comprises the use of compounds that are selective phospholipase C inhibitors for treating or ameliorating an inflammatory disorder. Another embodiment of the present invention comprises the use of compounds that are selective phospholipase C-β inhibitors useful for treating or ameliorating an inflammatory disorder.

Embodiments of the present invention include a method for treating or ameliorating an inflammatory disorder in a subject in need thereof comprising administering to the subject a therapeutically effective amount of a compound of formula (I) or composition thereof. An embodiment further includes a method for treating or ameliorating an inflammatory disorder in a subject in need thereof comprising administering to the subject a prophylactically effective amount of a compound of formula (I) or composition thereof.

The term "subject" as used herein, refers to an animal, preferably a mammal, most preferably a human, which has been the object of treatment, observation or experiment and is at risk of (or susceptible to) developing an inflammatory disorder or having an inflammatory disorder.

The term "administering" is to be interpreted in accordance with the methods of the present invention. Such methods include therapeutically or prophylactically administering an effective amount of a composition or medicament of the present invention at different times during the course of a therapy or concurrently in a combination form. Prophylactic administration can occur prior to the manifestation of symptoms characteristic of an inflammatory disorder such that the disorder is prevented or, alternatively, delayed in its progression. The methods of the present invention are further to be understood as embracing all therapeutic or prophylatic treatment regimens used by those skilled in the art.

The terms "therapeutically effective amount" or "prophylactically effective amount" refer to that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The term "inflammatory disorder" refers to disorders and diseases associated with an inflammatory response such that there is discomfort or decreased life expectancy to the organism. Such disorders and diseases occur in humans, and in various species of animals, and include, but are not limited to, autoimmune diseases (including but not limited to rheumatoid arthritis, systemic lupus erythematosus, inflammatory bowel diseases such as Crohn's disease and ulcerative colitis, multiple sclerosis, asthma, Graves' disease, myasthenia gravis, and ankylosing spondylitis); rejection of tissue or organ allografts (including but not limited to kidney, heart, liver, lung, whole pancreas, pancreatic islets, and corneas); infectious diseases (including but not limited to HIV-related diseases [eg AIDS] and tuberculosis); allergic diseases (including but not limited to hay fever, latex allergies, food allergies, and pet allergies); various inflammatory skin conditions (including but not limited to psoriasis, dermatis, eczema, poison ivy), neoplastic diseases (eg cancer), and vascular disorders (including but not limited to atherosclerosis and restenosis).

Another embodiment for use of the compounds of the present invention is a method for treating or ameliorating restenosis wherein a phospholipase inhibitor is impregnated on the surface of a medical device such as an angioplasty balloon or stent, thus targeting drug delivery to the local environment. Coronary angioplasty or stent implantation are otherwise highly effective procedures which reduce the severity of vascular abnormalities, but long-term success is limited by a high rate of restenosis. Accordingly, an example of a preferred use includes use of a phospholipase inhibitor on an angioplasty balloon or on a stent where restenotic endothelial and smooth muscle cell proliferation are the leading cause of vascular reocclusion.

An embodiment of the invention includes a composition or medicament comprising a mixture one or more compounds of the present invention and an optional pharmaceutically acceptable carrier.

The term "composition" refers to a product containing a compound of the present invention (such as a product comprising the specified ingredients in the specified amounts, as well as any product which results, directly or indirectly, from such combinations of the specified ingredients in the specified amounts). The term "medicament" refers to a product for use in treating or ameliorating an inflammatory disorder or condition mediated by PLC-β2.

The term "pharmaceutically acceptable" refers to molecular entities and compositions that are of sufficient purity and quality for use in the formulation of a composition or medicament of the present invention. Since both human use (clinical and over-the-counter) and veterinary use are equally included within the scope of the present invention, a formulation would include a composition or medicament for either human or veterinary use.

Embodiments include a process for making the composition or medicament comprising mixing any of the instant compounds and a pharmaceutically acceptable carrier and include those compositions or medicaments resulting from such a process. Contemplated processes include both conventional and unconventional pharmaceutical techniques. Other embodiments include a composition or medicament comprising a mixture of at least two of the instant compounds in association with a pharmaceutically acceptable carrier.

The composition or medicament may be administered in a wide variety of dosage unit forms depending on the method of administration; wherein such methods include (without limitation) oral, sublingual, nasal (inhaled or insufflated), transdermal, rectal, vaginal, topical (with or without occlusion), intravenous (bolus or infusion) or for injection (intraperitoneally, subcutaneously, intramuscularly, intratumorally or parenterally) using a suitable dosage form well known to those of ordinary skill in the area of pharmaceutical administration. Accordingly, the term dosage unit or dosage form is used to refer to (without limitation) a tablet, pill, capsule, solution, syrup, elixir, emulsion, suspension, suppository, powder, granule or sterile solution, emulsion or suspension (for injection [from an ampule or using a device such as an auto-injector] or for use as an aerosol, spray or drop). Furthermore, the composition may be presented in a form suitable for weekly or monthly administration: e.g. an insoluble salt of the active compound (such as the decanoate salt) may be adapted to provide a depot preparation for intramuscular injection.

In preparing a dosage form, the principal active ingredient (such as a compound of the present invention or a pharmaceutically acceptable salt thereof) is optionally mixed with one or more pharmaceutical carriers (such as a starch, sugar, diluent, granulating agent, lubricant, glidant, binder, disintegrating agent and the like), one or more inert pharmaceutical excipients (such as water, glycols, oils, alcohols, flavoring agents, preservatives, coloring agents, syrup and the like), one or more conventional tableting ingredient (such as corn starch, lactose, sucrose, sorbitol, talc, stearic acid, magnesium stearate, dicalcium phosphate, any of a variety of gums and the like) and a diluent (such as water and the like) to form a homogeneous composition (whereby the active ingredient is dispersed evenly throughout the mixture) which may be readily subdivided into dosage units containing equal amounts of a compound of the present invention.

Binders include, without limitation, starch, gelatin, natural sugars (such as glucose, beta-lactose and the like), corn sweeteners and natural and synthetic gums (such as acacia, tragacanth, sodium oleate, sodium stearate, magnesium stearate, sodium benzoate, sodium acetate, sodium chloride and the like). Disintegrating agents include, without limitation, starch, methyl cellulose, agar, bentonite, xanthan gum and the like.

Because of their ease of administration, tablets and capsules represent an advantageous oral dosage unit form, wherein solid pharmaceutical carriers are employed. If desired, tablets may be sugarcoated or enteric-coated by standard techniques. Tablets may also be coated or otherwise compounded to provide a prolonged therapeutic effect. For example, the dosage form may comprise an inner dosage and an outer dosage component, whereby the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and nonenteric layer or coating materials may be used (such as polymeric acids, shellacs, acetyl alcohol, cellulose acetate and the like) or combinations thereof.

The compound of formula (I) may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

As is also known in the art, the compounds may alternatively be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution or an isotonic aqueous saline solution. Other optional ingredients include vegetable oils (such as peanut oil, cottonseed oil, sesame oil and the like) and organic solvents (such as solketal, glycerol, formyl and the like). Alternatively, a sterile non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers or pain-soothing agents. Injectable suspensions may also be prepared, in which case appropriate liquid carriers, suspending agents and the like may be employed.

Compounds of the present invention may be administered intranasally using a suitable intranasal vehicle. Compounds of the present invention may be administered topically using a suitable topical transdermal vehicle or a transdermal patch. Administration via a transdermal delivery system requires a continuous rather than intermittent dosage regimen.

Compounds of the present invention may also be administered via a slow release composition; wherein, the composition includes a biodegradable slow release carrier (typically, a polymeric carrier) and a compound of the invention. Slow release carriers are well known in the art and are used to form particles that capture therein an active compound(s) and slowly degrade/dissolve in a suitable environment (e.g., aqueous, acidic, basic, etc). Such particles are useful because they degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter). In a process for preaparing a slow release composition, a slow release carrier and a compound of the invention are first dissolved or dispersed in an organic solvent. The resulting mixture is added into an aqueous solution containing an optional surface-active agent(s)to produce an emulsion. The organic solvent is then evaporated from the emulsion to provide a colloidal suspension of particles containing the slow release carrier and the compound of the invention.

As previously described, a contemplated embodiment of the dosage unit will contain an amount of an active ingredient or prodrug thereof necessary to be therapeutically effective for symptomatic relief to a subject in need thereof. A therapeutically effective amount of the active compound in the dosage unit may range from about 0.001 mg to about 1000 mg and may be constituted into any form suitable for the administration method and regimen selected for the subject. Depending on the subject and disease to be treated, the therapeutically effective amount may range from about 0.0001 mg/kg to 300 mg/kg of body weight per day; or, from about 0.0005 to about 100 mg/kg of body weight per day; or, from about 0.001 to about 50 mg/kg of body weight per day. An optimal therapeutically effective amount and administration method and regimen may be readily determined by those skilled in the art, and will vary depending on factors associated with the particular patient being treated (age, weight, diet and time of administration), the severity of the condition being treated, the compound and dosage unit being employed, the mode of administration and the strength of the preparation. Dosage unit(s) may be administered to achieve the therapeutically effective amount in a regimen of from about once per day to about 5 times per day. The preferred dosage unit for oral administration is a tablet containing, 0.01, 0.05, 0.1, 0.5, 1.0, 2.5, 5.0, 10.0, 15.0, 25.0, 50.0, 100, 150, 200, 250 or 500 mg of the active ingredient.

SYNTHETIC METHODS

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations have the indicated meanings:

| | |
|---|---|
| Ac-BSA or BSA | acylated bovine serum albumin or bovine serum albumin |
| Bn | benzyl |
| Cpd | compound |
| DIBAL | diisobutylaluminum hydride |
| DIC | 1,3-diisopropyl carbodiimide |
| DEAD | diethylazodicarboxylate |
| DMF | N,N-dimethyl formamide |
| DMSO | dimethyl sulfoxide |
| DPPF | 1,1'-bis(diphenylphosphini)ferrocene |
| EDIC | 1-(3-dimethylaminopropyl)-3-ethylcarbodiimide |
| Et | ethyl |
| HOBt | 1-hydroxybenzotriazole |
| LDA | lithium diisopropylamide |
| Me | methyl |
| min/h/rt/mp | minute/hour/room temperature/melting point |
| Ph or PH | phenyl |
| Pd$_2$(dba)$_3$ | tris(dibenzylideneacetone)dipalladium(0) |
| Py | pyridine |
| TFA | trifluoroacetic acid |
| THF | tetrahydrofuran |
| TMEDA | tetramethylethylenediamine |
| TPP | triphenylphosphine |

All commercially available chemicals were obtained from commercial suppliers and used without further purification. Particular components, such as the peptide reaction vessels (obtained from NovaBiochem), the Wang resin (also from Novabiochem, 70-90 mesh), Rink resin and the wrist action shaker (obtained from Burrell Scientific Co.) used in the examples are also commercially available.

Scheme A

Solid Phase Synthesis of Piperazinyl and Piperazinoyl Substituted Anilino Compounds In accordance with Scheme A, a commercially available Wang resin Compound A1 was reacted with a piperazine Compound A2 to provide a resin-bound Compound A3.

Other starting materials may also be used for both solid and solution based synthesis, thus providing a variety of equivalent substituent substitutions which are intended to be included within the scope of the present invention.

Compound A3 was coupled with a nitro substituted benzoic acid Compound A4 to yield a resin-bound Compound A5. The Compound A5 fluoro atom was replaced with Compound A6 (where n is preferably 1) to produce a piperazinyl-piperazinoyl substituted Compound A7. The Compound A7 nitro group was reduced to give the corresponding piperazinyl-piperazinoyl substituted anilino Compound A8. A compound such as an L$^2$ substituent moiety Compound A9 was coupled with Compound A8 to provide a Compound A10.

Cleavage of Compound A10 from the solid support resin yielded a Compound A11. The deprotected piperazinoyl nitrogen atom may be further substituted by reacting Compound A11 with an R$_2$ substituted coupling agent Compound A12 to provide a target Compound A13 representative of formula (I), (Ia), (Ib), (Ic) or (Id).

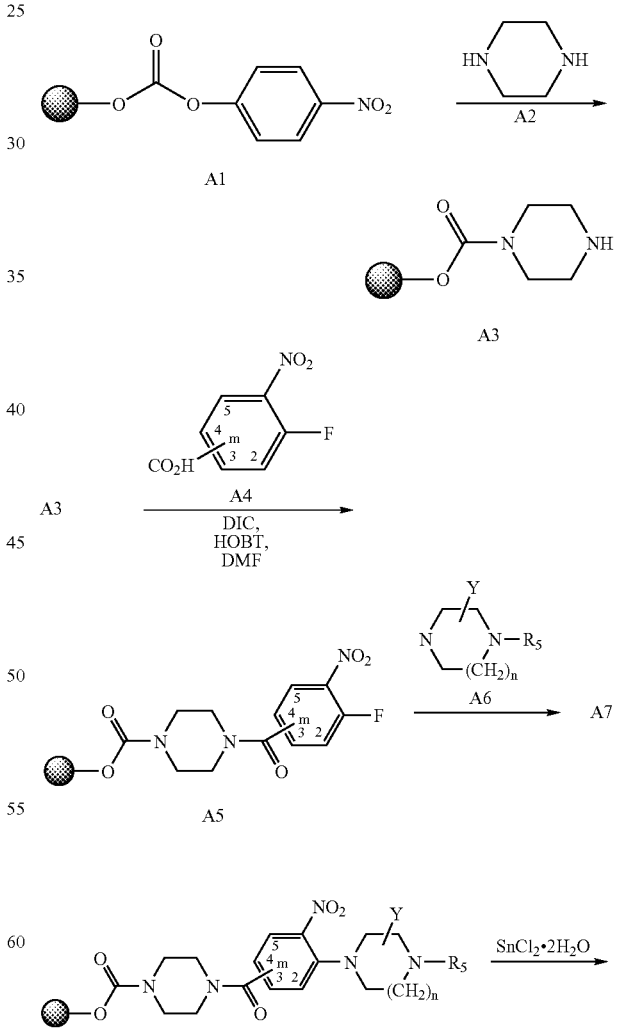

Scheme A

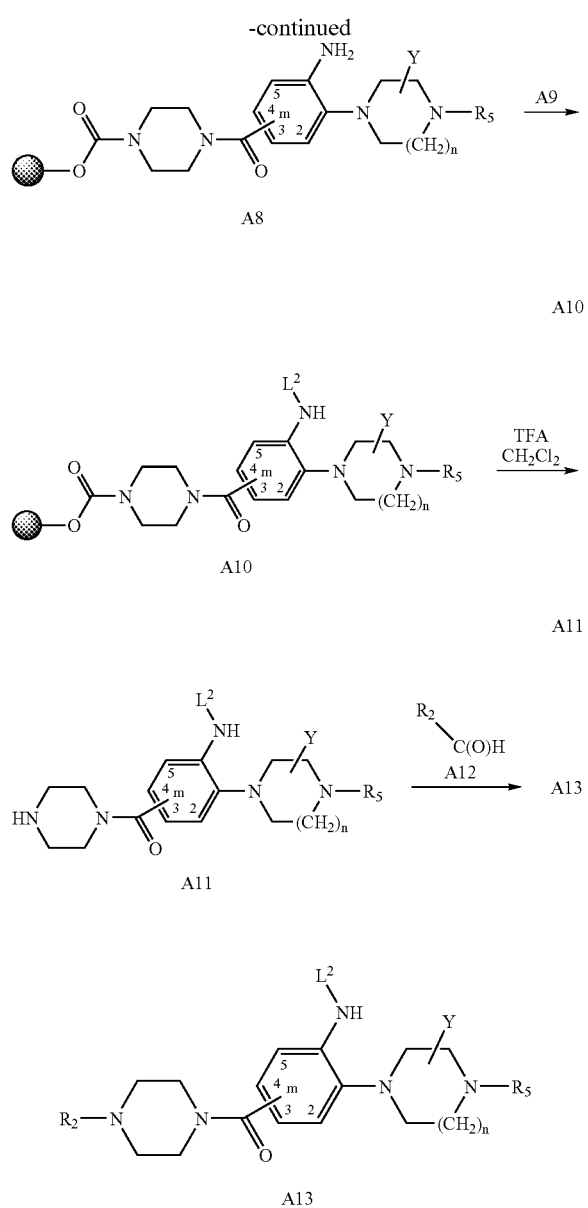

EXAMPLE 1

N-[2-[4-(diphenylmethyl)-1-piperazinyl]-5-(1-piperazinylcarbonyl)phenyl]-2-furancarboxamide (Cpd 3)

As shown in Scheme A for preparing a Compound A3, piperazine (35 mmol, 3.0 g) was added to a reaction vessel containing a commercially available p-nitrophenyl carbonate Wang resin (5.0 g, 3.0 mmol, 0.6 mmol/g) in DMF (50 mL). The reaction vessel used in this step was a tube fitted with a frit at the bottom and sealed with a screw-type cap. The mixture was shaken for 16 h using a wrist action shaker and the DMF was removed by vacuum filtration. The reaction product was sequentially washed with an excess of DMF and MeOH, then a final wash with $CH_2Cl_2$ until the filtrate did not exhibit a yellow color. A resin bound amine Compound A3 was obtained and used in the next step without characterization.

4-Fluoro-3-nitrobenzoic acid Compound 1a (2.82 g, 27 mmol) and 1-hydroxybenzotriazole (HOBT) (3.64 g, 27 mmol) were added in one portion to a 200 mL round bottom flask containing DMF (35 mL) and $CH_2Cl_2$ (35 mL). The solution was stirred under argon for 5 min and 1,3-diisopropylcarbodiimide (DIC) (4.2 mL, 27 mmol) was added dropwise. The mixture was then stirred for 30 min and added to the reaction vessel containing Compound A3. The mixture was shaken for 16 h and the solvent was removed by vacuum filtration. The reaction product was sequentially washed with an excess of DMF, $CH_2Cl_2$ and MeOH, then a final wash with $CH_2Cl_2$ to give a resin-bound methanone Compound 1b as a trifluoroacetate salt. To characterize Compound 1b, an aliquot of the washed product (15 mg) was cleaved from the resin using 5% TFA in $CH_2Cl_2$ (2 mL), shaken for 30 min and filtered, then sequentially washed with $CH_2Cl_2$ and MeOH and characterized: $^1H$ NMR $(CD_3OD)$ δ 3.22-3.54 (br m,4H), 3.60-4.08 (br m, 4H), 7.51-7.65 (m, 1H), 7.81-7.96 (m, 1H), 8.23-8.44 (m, 1H). ESMS m/z 254 ($M^+H$).

DMF (4 mL) and a 1-benzhydryl-piperazine Compound 1c (0.55 g, 2.2 mmol) were added to the reaction vessel containing Compound 1b (0.2 g, ~0.2 mmol), then diisopropylethylamine (0.174 mL, 1 mmol) was added. The mixture was shaken over a 2 day period and turned from a pale yellow color to a yellow-orange color, then the solvent was removed by vacuum filtration. The reaction product was sequentially washed with an excess of DMF, $CH_2Cl_2$ and MeOH, then a final wash with $CH_2Cl_2$ to give a resin-bound methanone substituted piperazinyl Compound 1d. To characterize Compound 1d, an aliquot of the washed product (20 mg) was cleaved from the resin using 50% TFA in $CH_2Cl_2$ (1 mL), shaken for 1 h and filtered, then washed with MeOH and characterized: ESMS m/z 531 ($M^+H$).

DMF (2 mL) and tin(II) chloride dihydrate (0.72 g, 3.2 mmol) were added in one portion to the reaction vessel containing Compound 1d (0.2 g, ~0.1 mmol). The mixture was shaken overnight and turned from a yellow-orange color to almost colorless, then the solvent was removed by vacuum filtration. The reaction product was sequentially washed with an excess of DMF, $CH_2Cl_2$ and MeOH, then a final wash with $CH_2Cl_2$ to give a resin-bound aminated Compound 1e. To characterize Compound 1e, an aliquot of the washed product (20 mg) was cleaved from the resin using 50% TFA in $CH_2Cl_2$ (1 mL), shaken for 1 h and filtered, then washed with MeOH and characterized: ESMS m/z 501 ($M^+H$); m/z 499 ($M^-H$).

Triethylamine (1.2 mmol, 0.15 mL) and a 2-furoyl chloride Compound 1f (0.08 mL) were added to the reaction vessel containing Compound 1e (0.10 mmol) and $CH_2Cl_2$ (5 mL). The mixture was shaken overnight and the solvent was removed by vacuum filtration. The reaction product was sequentially washed with an excess of DMF, $CH_2Cl_2$ and MeOH, then a final wash with $CH_2Cl_2$ to give a resin-bound amino substituted Compound 1 g. The washed Compound 1g was cleaved from the resin using 5% TFA in $CH_2Cl_2$ (20 mL), shaken for 30 min and filtered, then washed with $CH_2Cl_2$ and MeOH. The filtrates were combined and concentrated to provide Compound 3 (0.03 g, 44% yield) as a trifluoroacetate salt. ESMS m/e 550 ($M^+H$, 100%), 384 ($M$-$CHPh_2$, 100%).

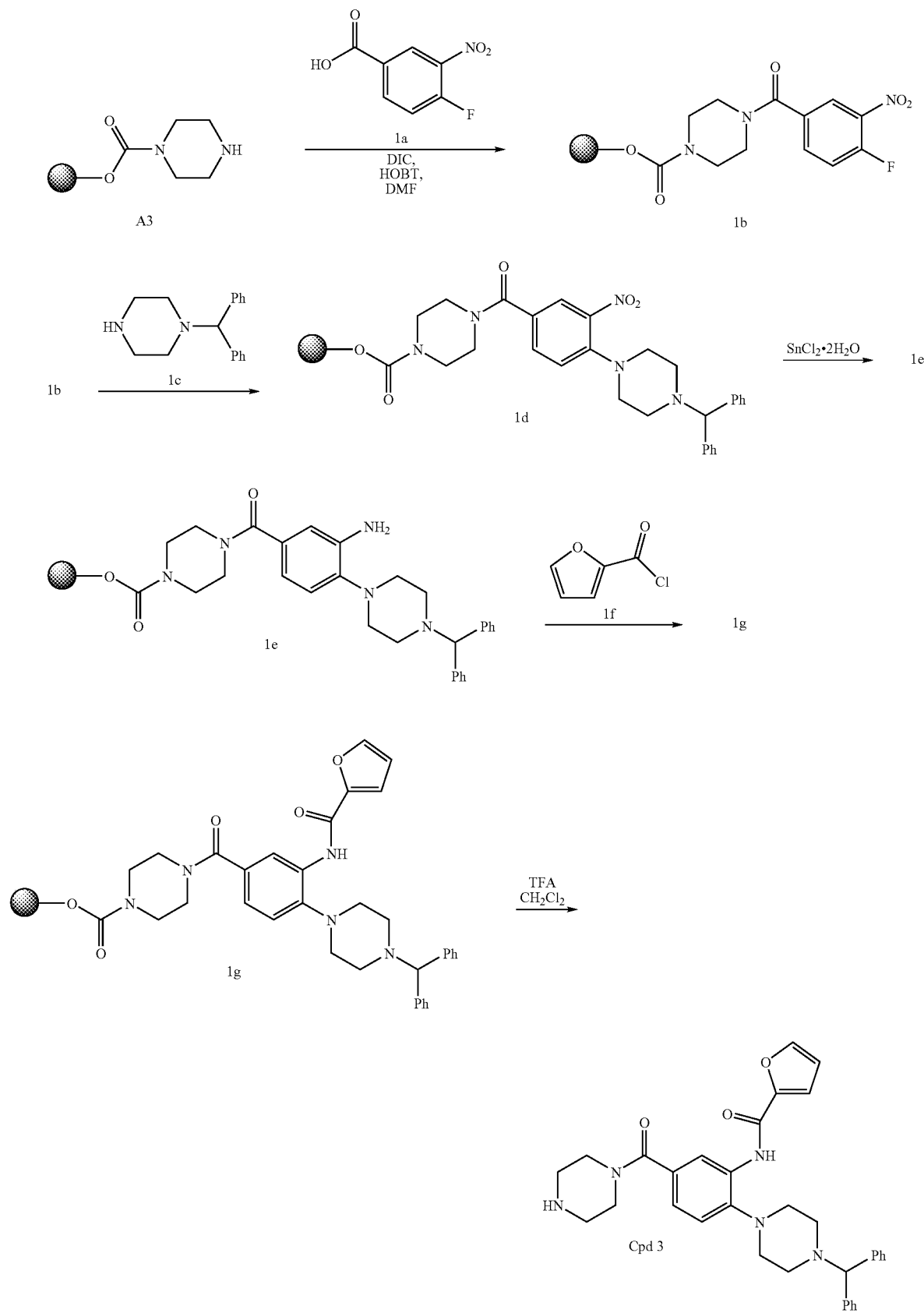

EXAMPLE 2

N-[2-[4-(diphenylmethyl)-1-piperazinyl]-5-(1-piperazinylcarbonyl)phenyl]-1-butanesulfonamide (Cpd 7)

Triethylamine (1.2 mmol, 0.15 mL) followed by a butanesulfonyl chloride Compound 2a (0.1 g) were added to a reaction vessel containing Compound 1e (0.11 mmol) and $CH_2Cl_2$ (5 mL). The mixture was shaken overnight and the solvent was removed by vacuum filtration. The reaction product was sequentially washed with an excess of DMF, $CH_2Cl_2$ and MeOH, then a final wash with $CH_2Cl_2$ to give a resin-bound amino substituted compound. The washed product was cleaved from the resin using 5% TFA in $CH_2Cl_2$ (20 mL), shaken for 30 min and filtered, then washed with $CH_2Cl_2$ and MeOH. The filtrates were combined and concentrated to provide Compound 7 (0.035 g, 47% yield) as a trifluoroacetate salt. ESMS m/e 576 ($M^+H$, 100%), 410 ($M-CHPh_2$, 80%).

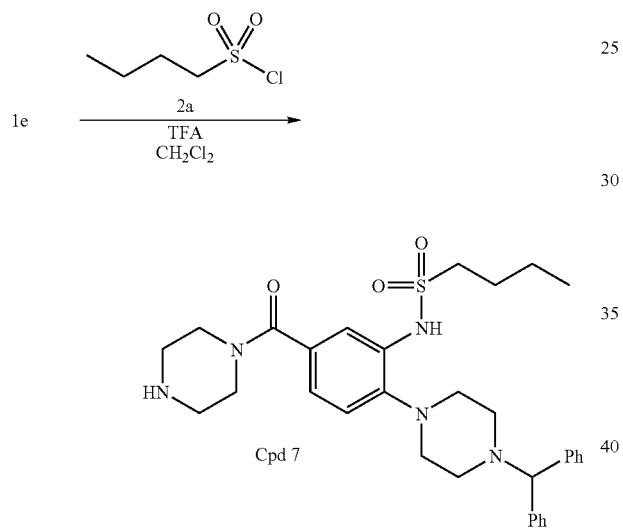

Using the procedures of the preceding examples and the appropriate reagents and starting materials known to those skilled in the art, other compounds of the present invention were also prepared including, but not limited to (MS: Mass Spec data as MS m/z $MH^+$):

| Cpd | Name | MS |
|---|---|---|
| 1 | N-[2-[4-(diphenylmethyl)-1-piperazinyl]-5-(1-piperazinylcarbonyl)phenyl]-4-methyl-benzamide | 574 |
| 2 | 5-(4-chlorophenyl)-N-[2-[4-(diphenylmethyl)-1-piperazinyl]-5-(1-piperazinylcarbonyl)phenyl]-2-methyl-3-furancarboxamide | 674 |
| 4 | N-[2-[4-(diphenylmethyl)-1-piperazinyl]-5-(1-piperazinylcarbonyl)phenyl]-propanamide | 512 |
| 5 | N-[2-[4-(diphenylmethyl)-1-piperazinyl]-5-(1-piperazinylcarbonyl)phenyl]-4-methyl-benzenesulfonamide | 610 |
| 6 | 4-chloro-N-[2-[4-(diphenylmethyl)-1-piperazinyl]-5-(1-piperazinylcarbonyl)phenyl]-benzenesulfonamide | 631 |
| 8 | N-[2-[4-(diphenylmethyl)-1-piperazinyl]-5-(1-piperazinylcarbonyl)phenyl]-methanesulfonamide | 534 |

Scheme B

Solution Phase Synthesis of Piperazinyl Substituted Anilino Compounds

Scheme B is an alternative to the solid phase synthesis method of Scheme A wherein Compound B1 was reacted with Compound A6 (where n is prefereably 1) to produce a Compound B2. Reduction of the Compound B2 nitro group gave the corresponding substituted anilino Compound B3. Compound A9 was reacted with Compound B3 to provide a target Compound B4 of formula (I).

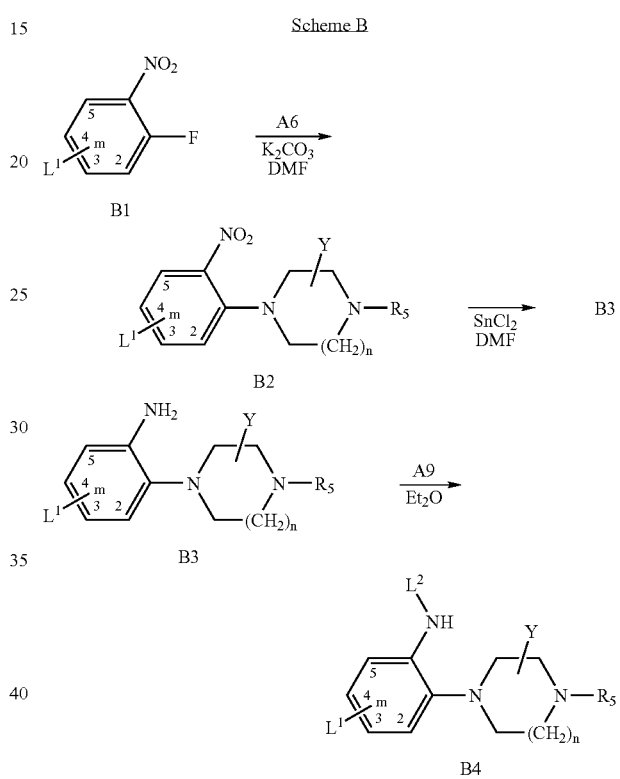

EXAMPLE 3

N-[2-[4-[bis(4-fluorophenyl)methyl]-1-piperazinyl]-5-(hydroxymethyl)phenyl]-N'-phenyl-urea (Cpd 10)

4-[4-[bis(4-fluorophenyl)methyl]-1-piperazinyl]-3-[[(phenylamino)carbonyl]amino]-benzoic acid methyl ester (Cpd 11)

Methyl 4-fluoro-3-nitrobenzoate Compound 3a (1.0 g, 5.02 mmol) (prepared as described in Nicolaou, et al., *Bioorg. Med. Chem.*, 1998, 1185), 1-[bis(4-fluorophenyl)methyl] piperazine Compound 3b (1.59 g, 5.52 mmol) and potassium carbonate (0.76 g, 5.52 mmol) were dissolved in N,N-Dimethylformamide (15 mL) and heated to about 80° C. for about 5 h then cooled to rt. The reaction mixture was diluted with ethyl acetate (100 mL), washed with brine (2×50 mL) and water (2×50 mL), then dried over $Na_2SO_4$, filtered and concentrated in vacuo to give 4-{4-[bis-(4-fluoro-phenyl)-methyl]-piperazin-1-yl}-3-nitro-benzoic acid methyl ester Compound 3c (2.4 g) as a yellow foam. MS m/z 468 ($M^+H$).

A mixture of the nitro substituted methyl ester Compound 3c (2.4 g, 5.13 mmol) and tin (II) chloride dihydrate (11.60 g, 51.34 mmol) was stirred in DMF (50 mL) for about 1 h. The reaction was diluted with ethyl acetate (100 mL), washed with brine (2×100 mL) and water (3×150 mL), then dried over $Na_2SO_4$, filtered and concentrated in vacuo to give 3-amino-4-{4-[bis-(4-fluoro-phenyl)-methyl]-piperazin-1-yl}-benzoic acid methyl ester Compound 3d (1.88 g) as a yellow foam. MS m/z 438 ($M^+H$).

A mixture of the amino substituted methyl ester Compound 3d (1.88 g, 4.30 mmol) and phenyl isocyanate Compound 3e (0.51 g, 4.30 mmol) was stirred in diethyl ether (50 mL) for about 18 h. The precipitate was collected by filtration, then washed with ether and hexane to provide Compound 11 (1.80 g) as an off-white solid. MS m/z 559 ($M^+H$).

A solution of Compound 11 (0.45 g, 0.81 mmol) and $LiAlH_4$ in THF (1.0 M, 1 mL, 1.0 mmol) in THF (10 mL) was stirred for about 18 h. The reaction was quenched with water (50 mL) and extracted with ethyl acetate (3×50 mL). The combined organic layers were washed with water (2×75 mL), dried over $Na_2SO_4$, filtered and concentrated in vacuo to give Compound 10 (0.31 g) as a white solid. MS m/z 529 ($M^+H$).

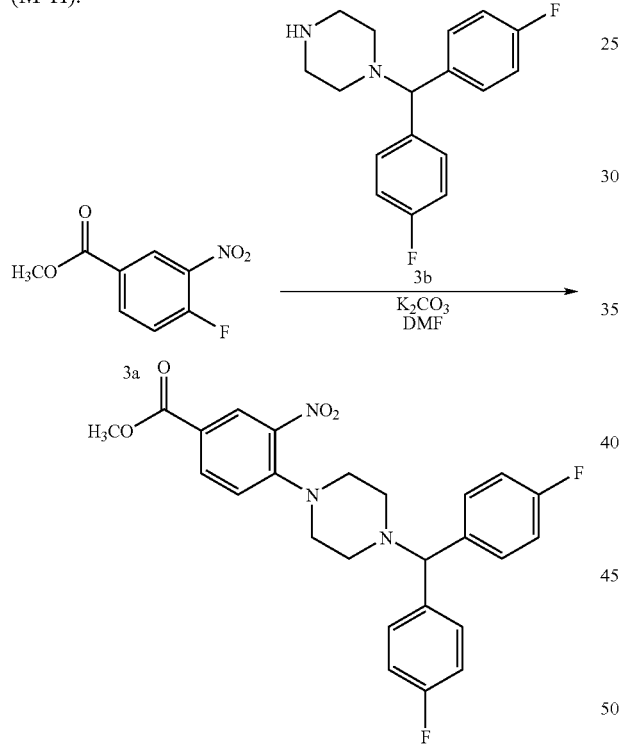

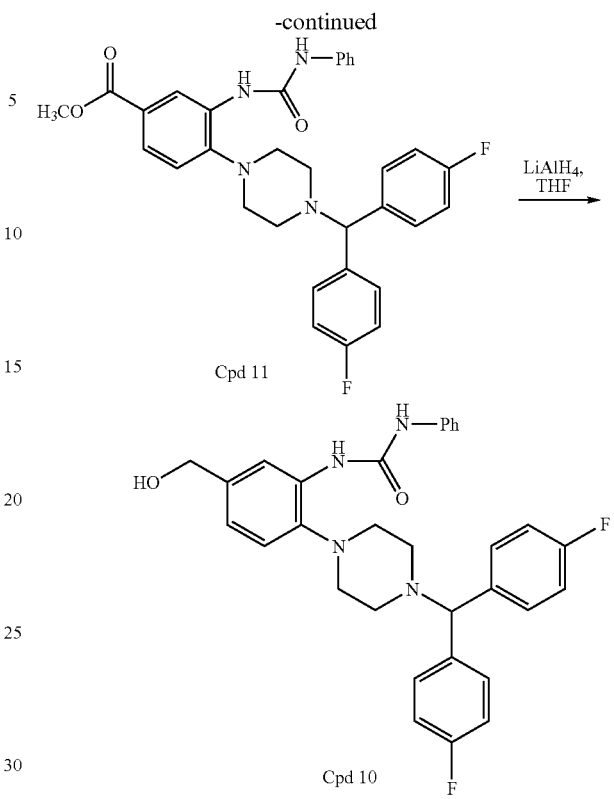

Using the-procedure of Example 3 and the appropriate reagents and starting materials known to those skilled in the art, other compounds of the present invention may be prepared including, but not limited to (MS: Mass Spec data as MS m/z $MH^+$):

| Cpd | Name | MS |
|---|---|---|
| 9 | N-[2-[4-(diphenylmethyl)-1-piperazinyl]-5-(methylsulfonyl)phenyl]-N'-phenyl-urea | 541 |

BIOLOGICAL EXAMPLES

The compounds of the present invention are useful PLC-β2 inhibitors. The following biological example demonstrates that the PLC-β2 inhibitor compounds of the present invention are useful in the treatment or amelioration of diseases and conditions affected by the modulation of phospholipase, including the aforementioned inflammatory disorders.

EXAMPLE 1

The hydrolysis of phosphatidylinositol-4,5-bisphosphate ($PIP_2$) by a specific phospholipase C-β2 (PLC-β2) produces two intracellular messengers, diacylglycerol (DAG) and inositol 1,4,5-trisphosphate ($IP_3$), which mediate the activation of protein kinase C and intracellular $Ca^{2+}$ release. A conventional organic solvent extraction method is widely used for PLC assays to isolate $IP_3$ from the substrate $PIP_2$. The conventional PLC-β2 assay, however, is terminated by addition of acidified organic solvents and subsequent extraction and phase separation. The conventional method does not allow for validation of PLC-β2 assay on robots for the high throughput screening of PLC-β2 inhibitors. Accordingly, a preferred method to test the compounds of the present invention, was developed utilizing a 96-well plate assay for PLC-β2 using immobilized radiolabeled substrate to quantitatively measure the reduction in the substrate level without a need for organic solvent extraction. The automated PLC-β2 assay described herein provides a convenient method for quantitative measurement of phospholipase C activities in a high throughput fashion.

Materials

Phospholipid FlashPlates and [$^3$H]PIP$_2$(20 Ci/mmol) were purchased from NEN Life Science Products (Boston, Mass. USA). BSA (acetylated), fatty acid-free BSA, sodium chloride, potassium chloride, PMSF, benzamidine, pepstatin A, calcium chloride, HEPES, and sodium deoxycholate were purchased from Sigma Chemical Co. (St. Louis, Mo. USA). DTT was purchased from Boehringer Mannheim (Indianapolis, Ind. USA). Q-Sepharose FF, Heparin-Sepharose CL-6B, and the Mono Q HR 5/5 column were purchased from Amersham-Pharmacia (Piscataway, N.J. USA). Bio-Gel HPHT column and Bio-Gel HPHT were from Bio-Rad Laboratories (Hercules, Calif. USA). HL-60 and Sf9 cells from *spodoptera frugiperda* (ATCC CRL-1711) were purchased from ATCC (Rockville, Md. USA). All other reagents were obtained from readily available commercial sources.

PLC Assay Using FlashPlates

Ninety-six well Phospholipid FlashPlates were coated with 0.2 mL of 50 mM Tris/HCl (pH 7.4), 0.01% Ac-BSA and 50,000 cpm of [$^{3H}$]PIP2 (phosphatidylinositol-4,5-bisphosphate) at 4° C. for 72 h. The wells were aspirated and washed twice with PBS. The reactions were conducted directly in the wells in PLC reaction buffer containing 50 mM Tris/HCl (pH 7.2), 2.75 mM EDTA (pH 7.3), 80 mM KCl, 10 mM LiCl, 0.04% DOC and 2 mM CaCl$_2$ in the absence or presence of the purified recombinant human PLC-β2 (prepared as described hereafter) or cytosolic human PLC-β2 from JL-60 cells. Reduction of radioactivity was monitored by a Packard TopCount instrument (Packard Instrument Company, Conn., USA).

Production of Recombinant PLC-β2 in Sf9 Cells

Suspension cultures of Sf9 cells were maintained in a spinner flask at 27° C. and stirred at 90 rpm. The cells were grown in Grace's media supplemented with 10% (v/v) fetal bovine serum, 3.3 g/l yeastolate, 3.3 g/l lactalbumin hydrosylate, glutamine (6.4 mM final), 50 pg/ml gentamicin, and 50 μg/ml kanamycin. Suspension of Sf9 cells (1.0×10$^6$ cells/ml) were infected with 5 pfu/cell of recombinant baculovirus encoding PLC-β2 and incubated at 27° C. for 72 h. The cells were collected by centrifugation (500×g, 7 min, 4° C.) and disrupted by hypotonic lysis buffer containing 20 mM Tris/HCl, pH 7.4, 5 mM MgCl$_2$, 2 mM EGTA, 200 βM PMSF, 200 βM benzamidine and 1 βM pepstatin A. The lysate was sonicated on ice and the nuclei and unbroken cells removed by centrifugation (500×g, 5 min, 4° C.). The supernatant was recovered and clarified by centrifugation (34,000 rpm, 60 min, 4° C.). The supernatant was used as a crude cytosolic fraction (Paterson, A., Boyer, J. L., Watts, V. J., Morris, A. J., Price, E. M., Harden, T. K. (1995) Concentration of enzyme-dependent activation of PLC β1 and PLC β2 by Gα$_{11}$ and βγ subunits. *Cellular Signalling* 7, 709-720).

Purification of Recombinant PLC-β2

Crude cytosol prepared from Sf9 cells expressing PLC-β2 was purified initially by chromatography on a 10 ml column of Q-Sepharose FF, equilibrated in buffer A (25 mM HEPES, pH 7.2, 2 mM DTT, 2 mM EDTA, 2 mM EGTA, 200 μM PMSF, 200 μM benzamidine, 1 μM pepstatin A containing 10 mM NaCl). The column was washed with 20 ml of equilibration buffer and eluted with a 200-ml gradient of 110-410 mM NaCl in buffer A. The fractions containing PLC activity were pooled and diluted with buffer A. The diluted enzyme was applied to a 4 ml column of heparin-SepharoseCL-6B equilibrated in buffer A and the column washed with 70 ml of buffer A. The column was eluted with 80 ml of gradient of 0-1.0 M NaCl in buffer A, the column eluate collected in 3 ml fractions. The fractions containing PLC activity were pooled and diluted in buffer B (25 mM HEPES pH 7.2, 10 mM KCl, 2 mM DTT, 200 μM PMSF, 200 μM benzamidine, 1 μM pepstatin A) and applied to a Bio-Gel HPHT (10 ml) hydroxylapatite column operated in conjunction with a Bio-Gel HPHT and equilibrated in buffer B. The column was washed with 20 ml of buffer B and PLC-β2 eluted with a gradient of 0-500 mM potassium phosphate in buffer B. The fractions containing PLC activity were pooled, diluted with buffer A containing 10 mM NaCl and applied to an FPLC Mono Q HR 5/5 column equilibrated in buffer A. The column was washed with 5.0 ml of equilibration buffer and then eluted with a 10 ml gradient of 0.01-1.0 M NaCl in buffer A. The column eluate was collected in 0.5 ml fractions. The fractions containing PLC activity were pooled and diluted in buffer A containing 20% glycerol and stored at −80° C.

Cell Culture and Preparation of Cytosolic PLC

HL-60 cells were grown in suspension and induced to differentiate into mature myeloid forms by addition of 1.25% (v/v) DMSO to the culture medium. Differentiated cells were pelleted by centrifugation, resuspended in 200 ml of lysis buffer containing 250 mM sucrose, 20 mM Tris-HCl, pH 7.5, 1.5 mM MgCl$_2$, 1 mM ATP, 3 mM benzamidine, 1 μM leupeptin, 1 mM PMSF and 2 μg/ml of soybean trypsin inhibitor (Camps, M., Hou, C., Jakobs, K. H., and Gierschik, P. (1990) Guanosine 5'-[γ-thio]triphosphate-stimulated hydrolysis of phosphatidylinositol 4,5-bisphosphate in HL-60 granulocytes. *Biochem. J.* 271, 743-748). Cells were homogenized by nitrogen cavitation. Cytosol was prepared from the post-nuclear supernatant by sequential centrifugation. In some cases, cytosol was concentrated by pressure filtration in a stirred cell equipped with an Amicon PM 10 membrane.

Purification of βγ Subunits of Retinal Transducin

Retinal rod outer segment membranes were prepared from bovine eyes as described in Camps, M., Hou, C., Sidroupoulos, D., Stock, J. B., Jakobs, K. H., Gierschik, P., (1992) Stimulation of phospholipase C by guanine-nucleotide-binding protein βγ subunits. *Eur. J. Biochem.* 206, 821-831. Transducin was eluted from the membranes with buffer containing 100 μM GTP and used for the subunit preparation procedure without delay. Transducin was resolved into α$_t$ and βγ$_t$ subunits by chromatography on Blue Sepharose CL-6B using a FPLC equipment (Pharmacia). Fractions containing βγ$_t$ subunits were pooled and concentrated about 20-fold by centrifugation using a CentriCon 10 PM (Amicon). The purified protein was snap-frozen in liquid nitrogen and stored at −80° C.

Results

The results for compounds of the present invention are shown in the following table:

| Cpd | IC$_{50}$(µM) |
|---|---|
| 1 | 12.6 |
| 2 | 17.4 |
| 3 | 21.6 |
| 4 | >25 |
| 5 | 10.8 |
| 6 | 8.7 |
| 7 | >25 |
| 8 | 9.8 |
| 9 | >10 (60% Inh.) |
| 10 | >10 (47% Inh.) |
| 11 | >10 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound selected from the group consisting of:
N-[2-[4-(diphenylmethyl)-1-piperazinyl]-5-(1-piperazinylcarbonyl)phenyl]-4-methyl-benzamide;
5-(4-chlorophenyl)-N-[2-[4-(diphenylmethyl)-1-piperazinyl]-5-(1-piperazinylcarbonyl)phenyl]-2-methyl-3-furancarboxamide;
N-[2-[4-(diphenylmethyl)-1-piperazinyl]-5-(1-piperazinylcarbonyl)phenyl]-2-furancarboxamide; and
N-[2-[4-(diphenylmethyl)-1-piperazinyl]-5-(1-piperazinylcarbonyl)phenyl]-propanamide.

2. A composition comprising a pharmaceutically acceptable carrier, excipient, tableting ingredient or diluent and the compound of claim 1.

* * * * *